(12) United States Patent
Demares et al.

(10) Patent No.: US 9,986,735 B2
(45) Date of Patent: Jun. 5, 2018

(54) COMPOSITIONS AND METHODS FOR ENHANCING MICROBIAL STABILITY

(71) Applicants: NOVOZYMES BIOAG A/S, Bagsvaerd (DK); NOVOZYMES BIOLOGICALS, INC., Salem, VA (US)

(72) Inventors: Diego Omar Demares, Buenos Aires (AR); Florencia Olivieri, Buenos Aires (AR); Gabriel Osvaldo Gutkind, Buenos Aires (AR)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days. days.

(21) Appl. No.: 14/780,318

(22) PCT Filed: Mar. 27, 2014

(86) PCT No.: PCT/US2014/031952
§ 371 (c)(1),
(2) Date: Sep. 25, 2015

(87) PCT Pub. No.: WO2014/160827
PCT Pub. Date: Oct. 2, 2014

(65) Prior Publication Data
US 2016/0050915 A1    Feb. 25, 2016

Related U.S. Application Data

(60) Provisional application No. 61/806,093, filed on Mar. 28, 2013.

(51) Int. Cl.
*A01N 25/32* (2006.01)
*A01N 47/00* (2006.01)
*A01N 63/00* (2006.01)
*C12N 1/04* (2006.01)
*A01C 1/06* (2006.01)

(52) U.S. Cl.
CPC ............. *A01N 25/32* (2013.01); *A01N 47/00* (2013.01); *A01N 63/00* (2013.01); *C12N 1/04* (2013.01); *A01C 1/06* (2013.01)

(58) Field of Classification Search
None
See application file for complete search history.

(56) References Cited

U.S. PATENT DOCUMENTS

| | | | |
|---|---|---|---|
| 4,149,869 A | 4/1979 | Lloyd | |
| 5,026,417 A | 6/1991 | Kucey | |
| 5,106,648 A | 4/1992 | Williams | |
| 5,484,464 A | 1/1996 | Gleddie | |
| 5,916,029 A | 6/1999 | Smith | |
| 8,020,343 B2 | 9/2011 | Pearce | |
| 2001/0021711 A1* | 9/2001 | Beilfuss | A01N 43/80 514/245 |
| 2008/0132411 A1 | 6/2008 | Watt | |
| 2010/0099560 A1 | 4/2010 | Hnatowich | |
| 2012/0208699 A1 | 8/2012 | Pearce | |

FOREIGN PATENT DOCUMENTS

| | | |
|---|---|---|
| EP | 0454291 A1 | 2/1991 |
| WO | 94/06732 A1 | 3/1994 |
| WO | 2006/071369 A2 | 7/2006 |

OTHER PUBLICATIONS

Syngenta. "Apron Maxx RFC", Syngenta Canada Inc.: Guelph, ON, 2014; pp. 1-8.*

* cited by examiner

*Primary Examiner* — Michelle F. Paguio Frising
(74) *Attorney, Agent, or Firm* — Adam Rucker

(57) ABSTRACT

Described herein are compositions and methods for increasing the survivability of one or more beneficial microorganisms.

9 Claims, No Drawings

US 9,986,735 B2

COMPOSITIONS AND METHODS FOR ENHANCING MICROBIAL STABILITY

CROSS-REFERENCE TO RELATED APPLICATIONS

This application is a 35 U.S.C. 371 national application of PCT/US2014/031952 filed Mar. 27, 2014, which claims priority or the benefit under 35 U.S.C. 119 of U.S. provisional application No. 61/806,093 filed Mar. 28, 2013, the contents of which are fully incorporated herein by reference.

FIELD

Compositions and methods for enhancing the stability of microorganisms, particularly when microorganisms are applied to seeds.

BACKGROUND

Plant growth depends at least in part on interactions between the plant and microorganisms that habitate the surrounding soil. For example, the symbiosis between the gram-negative soil bacteria, Rhizobiaceae and Bradyrhizobiaceae, and legumes such as soybean, is well documented. The biochemical basis for these relationships includes an exchange of molecular signaling, wherein the plant-to-bacteria signal compounds include flavones, isoflavones and flavanones, and the bacteria-to-plant signal compounds, which include the end products of the expression of the bradyrhizobial and rhizobial nod genes, known as lipo-chitooligosaccharides (LCOs). The symbiosis between these bacteria and the legumes enables the legume to fix atmospheric nitrogen for plant growth, thus obviating a need for nitrogen fertilizers. Since nitrogen fertilizers can significantly increase the cost of crops and are associated with a number of polluting effects, the agricultural industry continues its efforts to exploit this biological relationship and develop new agents and methods for improving plant yield without increasing the use of nitrogen-based fertilizers.

Another known and well studied symbiotic association between plants and soil microorganisms involves arbuscular mycorrhizal (AM) fungi. This group of fungi, recently renamed Glomeromycota, is widely distributed throughout the plant kingdom including angiosperms, gymnosperms, pteridophytes and some bryophytes (Smith and Read, 2008). Among the angiosperms, at least 80% of the species can form AM symbioses, the only major exceptions being Brassicaceae and Chenopodiaceae. Arbuscular mycorrhizal fungi are able to transfer rare or poorly soluble mineral nutrients such as phosphorus, zinc and copper from the soil to the plant, which in turn provides carbohydrates to the fungus. This exchange of nutrients can be of critical importance when soil fertility and water availability are low, conditions that severely limit agricultural production in most parts of the world (Smith, et al., Mycorrhizal symbiosis. 787 pp., Academic Press. (2008)).

In addition to symbiotic relationships with microorganisms, healthy growth requires plants to extract a variety of elements such as phosphorus and micronutrients (copper, iron, zinc, etc) from the soil. Soils can oftentimes be deficient in these elements or contain forms of the elements that cannot be readily assimilated by the plant. Fertilizers are typically applied to soils to increase the amount of phosphorus for plant uptake. However, the vast majority of the phosphorus applied is rapidly converted to forms that cannot be utilized by the plant. Various fungal strains of *Penicillium* (e.g., *P. bilaiae*) and *Rhizobium* spp. have been applied to soil to facilitate uptake of phosphorus by the plant. See, e.g., U.S. Pat. Nos. 5,026,417 and 5,484,464 and U.S. Patent Application Publication 2010/0099560.

Continuing efforts are made to exploit these types of relationships between plants and microorganisms with the goal of increasing plant growth and yield. One such effort is in the field of inoculants with specific efforts being devoted to enhancing "on-seed" inoculant technologies and in particular, to enhancing the survivability of inoculants once they are applied to a seed. One such cause accounting for low survivability of inoculants include, among other things, the presence of incompatible compounds existing in seed treatments. Such compounds may include preservatives or other biocides used in seed treatment ingredients.

U.S. Pat. No. 4,149,869 discloses seeds coated with a mixture containing a caseinate salt and viable *rhizobia* bacteria.

EP. Pat. App. Pub. No. 0454291 discloses a process for producing an enhanced *Rhizobium* inoculant.

U.S. Pat. No. 5,106,648 discloses a method for coating seeds, however, the disclosure states that it is necessary to use Rhizobial strains that are resistant to fungicides to allow seeds to be coated with fungicides at the same time.

U.S. Pat. App. Pub. No. 2008/0132411 discloses a method for improving the survival and viability of microorganism inoculants on the seeds comprising the step of coating seeds with a mixture comprising a carbohydrate, a sugar alcohol, and microorganisms.

U.S. Pat. App. Pub. No. 2012/0208699 discloses methods and compositions for reducing the bridging of treated seeds, including some that also enhance the survivability of any beneficial microorganisms included in the composition or mixes therewith and/or enhance the yield of the plants that grow from the seed to which the treatment is applied.

Pat. App. Pub. No. WO 1994/06732 discloses a method obtaining a wettable powder inoculant formulation for use with leguminous crops.

Pat. App. Pub. No. WO 2006/071369 discloses a method for producing a liquid inoculant containing a desiccant, wherein the method can improve the survival and stability of bacteria in liquid inoculants in pack and on seeds.

Dey, B. P., Engley Jr., F. B., (1994). Neutralization of antimicrobial chemicals by recovery media. *J. Microbiol. Methods*. 19: 51-58 (discloses the ability to neutralize a variety of antimicrobial agents using a neutralizing medium to recover *Staphylococcus aureus* strain ATCC 6532 from tile surfaces exposed to a commercial pphenol and a quaternary ammonium compound).

A need remains, however, for compositions and methods that can enhance the survivability of microorganisms when compounds that are not compatible with microbially based inoculants are used as part of a seed treatment.

SUMMARY

Described herein are compositions that increase the survivability of one or more microorganisms comprising at least one compound comprising one or more microbially stabilizing compounds and at least one second ingredient selected from groups (A) to (E) wherein group (A) is a fungicide, group (B) is an insecticide, group (C) is a nematicide, group (D) is an acaricide, group (E) is an herbicide, and group (F) is a fertilizer. In one embodiment, the one or more microbially stabilizing compounds may comprise a compound selected from the group consisting of yeast extract, calcium caseinate, milk, urea, hematinic agents, beef extract, ammonia, amino acids, ammonium salts, ferric salts, ferrous salts, gluconolactone, glutathione, lecithin, polysorbates, albumin, peptones (e.g., soy peptones), and combinations thereof.

In another embodiment, the composition comprises one or more agriculturally beneficial ingredients, such as one or more biologically active ingredients. Biologically active ingredients may include one or more plant signal molecules or one or more beneficial microorganisms. In a specific embodiment, the one or more biologically active ingredients may include one or more lipo-chitooligosaccharides (LCOs), one or more chitooligosaccharides (COs), one or more chitinous compounds, one or more flavonoids, one or more non-flavonoid nod gene inducers and derivatives thereof, one or more karrikins and derivatives thereof, or any signal molecule combination thereof. In another embodiment, the one or more beneficial microorganisms Further described herein is a method for increasing the survivability of one or more microorganisms. In one embodiment, the method for increasing the survivability of one or more microorganisms comprises adding to a seed treatment composition one or more microbially stabilizing compounds which inhibit the antimicrobial activity of one or more antimicrobial compounds and adding one or more microorganisms to the seed treatment composition. In an embodiment, the one or more microbially stabilizing compounds may include yeast extract, calcium caseinate, milk, urea, hematinic agents, beef extract, ammonia, amino acids, ammonium salts, ferric salts, ferrous salts, gluconolactone, glutathione, lecithin, polysorbates, albumin, peptones, and combinations thereof. In another embodiment the one or more antimicrobial compounds may include a bacteriostat, a bactericide, or a combination thereof.

Finally, a method for coating a seed is described herein. In an embodiment, the methods comprises adding to a seed treatment composition one or more microbially stabilizing compounds which inhibit the antimicrobial activity of one or more antimicrobial compounds, adding one or more microorganisms to the seed treatment composition, and applying the seed treatment to a seed.

DETAILED DESCRIPTION

The disclosed embodiments relate to compositions and methods for enhancing plant growth.

Definitions

As used herein, the singular forms "a", "an" and "the" are intended to include the plural forms as well, unless the context clearly indicates otherwise.

As used herein, "microbially stabilizing compound(s)" means any compound capable of maintaining and/or increasing the viability, survivability, and/or CFU of one or more microbes. As used herein a "microbially stabilizing compound(s)" is further intended to mean any compound capable of preventing and/or decreasing the amount of death and/or rate of death of one or more microbes.

As used herein, the term "dairy substrate" means the milk of an animal, as well as components of the milk (e.g., cream), and combinations of milk and cream (e.g., half and half). As used herein, the term "milk" means whole milk produced by an animal, as well as processed forms thereof. Indeed, any suitable form of milk finds use in the present embodiments, including milk that includes or does not include whey, as well as whole milk, raw milk, skim milk, evaporated milk, reconstituted milk, condensed milk, pasteurized milk, unpasteurized, homogenized, non-homogenized, or re-hydrated milk powder.

As used herein the term "urea" means an organic compound with the chemical formula $NH_2CONH_2$ as well as isomers, salts, solvates, and derivatives thereof.

As used herein, the term "amino acid" means naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid also refers to poly(amino acid) such as peptides, polypeptide and proteins.

"Amino acid analogs" means compounds that have the same basic chemical structure as a naturally occurring amino acid, i.e., a carbon that is bound to a hydrogen, a carboxyl group, an amino group, and an R group. Examples of amino acid analogs include, but are not limited to, homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily, have the same basic structure as a naturally occurring amino acid. Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" mean chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "gluconolactone" means molecules having the molecular formula $C_6H_{10}O_6$, a molar mass of about 178.14 g mol$^{-1}$, and the structure

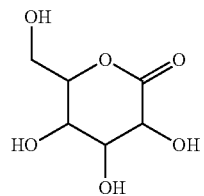

and includes isomers, salts, and solvates thereof.

As used herein, the term "glutathione" means molecules having the the molecular formula $C_{10}H_{17}N_3O_6S$, a molar mass of about 307.32 g mol$^{-1}$, and the structure

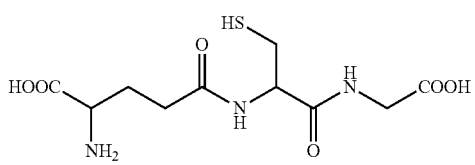 [SMILES: NC(CCC(=O)NC(CS)C(=O)NCC(=O)O)C(=O)O]

and includes isomers, salts, and solvates thereof.

As used herein, the term "lecithin" means a phosphatide mixture. The term lecithin as used herein without a modifying adjective may refer to either or both of the acylated and non-acylated forms of lecithin.

As used herein, the term "polysorbate" means oleate esters of sorbitol and its anhydrides, typically copolymerized with ethylene oxide.

As used herein, the term "albumin" is used interchangeably with "serum albumin" and is not meant to define the source of the albumin. The term "albumin" as used herein includes any derivatives of albumin or modified versions of albumin. Thus, the term "albumin" as used herein may refer either to albumin purified from a natural source such as blood or serous fluids, or it may refer to chemically synthesized or recombinantly produced albumin or albumin variants or derivatives of native albumins.

As used herein, "stable" is a term that is known in the art, and in an aspect, stable is means the ability of the microorganism to remain in a viable form until it is applied as disclosed herein (e.g., to a plant and/or plant part, to enhance the growth of a plant and/or plant part, enhance seed germination, enhance seedling emergence, enhance nitrogen fixation, enhance phosphate solubilization, etc.).

As used herein, the term "agriculturally beneficial ingredient(s)" means any agent or combination of agents capable of causing or providing a beneficial and/or useful effect in agriculture.

As used herein, "biologically active ingredient(s)" means biologically active ingredients (e.g., plant signal molecules, other microorganisms, etc.) other than the bacterially stabilizing compound described herein.

As used herein the terms "signal molecule(s)" or "plant signal molecule(s)", which may be used interchangeably with "plant growth-enhancing agent(s)," broadly means any agent, both naturally occurring in plants or microbes, and synthetic (and which may be non-naturally occurring) that directly or indirectly activates or inactivates a plant biochemical pathway, resulting in increased or enhanced plant growth, compared to untreated plants or plants harvested from untreated seed.

As used herein, the terms "effective amount", "effective concentration", or "effective dosage" means the amount, concentration, or dosage of the one or more microbially stabilizing compounds sufficient to inhibit the antimicrobial activity of one or more compounds. The actual effective dosage in absolute value depends on factors including, but not limited to, the amount (e.g., the concentration, volume, of antimicrobial compound, etc.) of antimicrobial compound to be inhibited, synergistic or antagonistic interactions between the other active or inert ingredients which may increase or reduce the antimicrobial inhibiting effects/activity of the one or more microbially stabilizing compounds, and the stability of the one or more microbially stabilizing compounds in compositions and/or as plant or plant part treatments. The "effective amount", "effective concentration", or "effective dosage" of the one or more microbially stabilizing compounds may be determined, e.g., by a routine dose response experiment.

As used herein, the term "carrier" means an "agronomically acceptable carrier." An "agronomically acceptable carrier" means any material which can be used to deliver the actives (e.g., microbially stabilizing compounds described herein, agriculturally beneficial ingredient(s), biologically active ingredient(s), etc.) to a plant or a plant part (e.g., a seed), and preferably which carrier can be applied (to the plant, plant part (e.g., a seed), or soil) without having an adverse effect on plant growth, soil structure, soil drainage or the like.

As used herein, the term "nutrient(s)" means any nutrient (e.g., vitamins, macrominerals, micronutrients, trace minerals, organic acids, etc.) which are needed for plant growth, plant health, and/or plant development.

As used herein, the term "biostimulant(s)" means any agent or combination of agents capable of enhancing metabolic or physiological processes within plants and soils.

As used herein, the term "herbicide(s)" means any agent or combination of agents capable of killing weeds and/or inhibiting the growth of weeds (the inhibition being reversible under certain conditions).

As used herein, the term "fungicide(s)" means any agent or combination of agents capable of killing fungi and/or inhibiting fungal growth.

As used herein, the term "insecticide(s)" means any agent or combination of agents capable of killing one or more insects and/or inhibiting the growth of one or more insects.

As used herein, the term "nematicide(s)" means any agent or combination of agents capable of killing one or more nematodes and/or inhibiting the growth of one or more nematodes.

As used herein, the term "acaricide(s)" means any agent or combination of agents capable of killing one or more acarids and/or inhibiting the growth of one or more acarids.

As used herein, term "enhanced plant growth" means increased plant yield (e.g., increased biomass, increased fruit number, increased boll number, or a combination thereof that may be measured by bushels per acre), increased root number, increased root mass, increased root volume, increased leaf area, increased plant stand, increased plant vigor, faster seedling emergence (i.e., enhanced emergence), faster germination, (i.e., enhanced germination), or combinations thereof.

As used herein, the terms "plant(s)" and "plant part(s)" means all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material and vegetative and generative propagation material (e.g., cuttings, tubers, rhizomes, offshoots and seeds, etc.).

As used herein, the term "inoculum" means any form of microbial cells, or spores, which is capable of propagating on or in the soil when the conditions of temperature, moisture, etc., are favorable for microbial growth.

As used herein, the term "nitrogen fixing organism(s)" means any organism capable of converting atmospheric nitrogen ($N_2$) into ammonia ($NH_3$).

As used herein, the term "phosphate solubilizing organism" means any organism capable of converting insoluble phosphate into a soluble phosphate form.

As used herein, the terms "spore" has its normal meaning which is well known and understood by those of skill in the art. As used herein, the term spore means a microorganism in its dormant, protected state.

As used herein, the term "source" of a particular element means a compound of that element which, at least in the soil conditions under consideration, does not make the element fully available for plant uptake.

Compositions

The compositions disclosed comprise one or more microbially stabilizing compounds as described herein. In certain embodiments, the composition may be in the form of a liquid, a gel, a slurry, a solid, or a powder (wettable powder or dry powder).

In a particular embodiment, the one or more microbially stabilizing compounds are compounds capable of inhibiting the activity of one or more antimicrobial compounds.

As used herein, the term "anti-microbial compound(s)" includes a biocide (i.e., a bacteriostats or a bactericides). Non-limiting examples of biocides include the following:

Bactericides:

As used herein, a bactericide is an agent that kills bacteria. A bactericide may be a disinfectant, antiseptic or antibiotic.

Non-limiting examples of a bactericidal disinfectant may be:

active chlorine (i.e., hypochlorites, chloramines, dichloroisocyanurate and trichloroisocyanurate, wet chlorine, chlorine dioxide, etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride, etc.), strong oxidizers, such as ozone and permanganate solutions;

heavy metals and their salts, such as colloidal silver, silver nitrate, mercury chloride, phenylmercury salts, copper sulfate, copper oxide-chloride, etc. Heavy metals and their salts are the most toxic, and environment-hazardous bactericides and therefore, their use is strongly oppressed or eliminated; further, also properly concentrated strong acids (phosphoric, nitric, sulfuric, amidosulfuric, toluenesulfonic acids) and alkalis (sodium, potassium, calcium hydroxides), such as of pH<1 or >13, particularly under elevated temperature (above 60° C.), kills bacteria.

Non-limiting examples of a bactericidal antiseptic may be:

properly diluted chlorine preparations (e.g., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

Non-limiting examples of a bactericidal antibiotic may be penicillin, cephalosporins, and aminoglycosidic antibiotics.

Other bactericidal antibiotics include the fluoroquinolones, nitrofurans, vancomycin, monobactams, co-trimoxazole, and metronidazole.

Preferred bactericides are:

Halogen containing compounds such as:
  Bronopol—active 2-bromo-2-nitro-1,3-propanadiol
  Dowicil 75—active 1-(3-chloroallyl)-3,5,7-triaza-1-azoniaadamantane chloride
  DBNPA—active dibromonitrilopropionamide
OrganoSulfurs—includes Isothaizolones such as:
  Proxel (Nipacide)—active 1,2-benzisothiazolin-3-one
  Kathon—active 5-chloro-2-methyl-4-isosthiazolin-3-one, 2-methyl-4-isosthiazolin-3-one
Nitrogen containing compounds such as:
  Germall II (Diazolidinyl urea)
  Tris nitro (tris(hydroxymethyl)nitromethane)
Phenolics such as:
  Dowicide (sodium o-phenylphenate)
  Preventol D2® (benzyl-hemiformal)
Inorganics such as:
  copper arsenates
  cuprous oxide
Organometallics such as:
  compounds of arsenic, copper, mercury
Quaternary ammonium compounds.

Bacteriostats:

As used herein, a bacteriostat is an agent, usually chemical, that prevents the growth of bacteria but that does not necessarily kill them or their spores. Upon removal of the bacteriostat, the bacteria usually start to grow again.

Non-limiting examples of bacteriostats include sodium azide and thimerosol.

Microbially Stabilizing Compounds:

The microbially stabilizing compounds described herein may include any compound that is capable of increasing the survivability of one or more microorganisms. In one embodiment, the one or more microbially stabilizing compounds inhibit the activity of one or more of the biocides described herein. In another embodiment, the one or more microbially stabilizing compounds inhibit the activity of one or more of the bactericides disclosed herein. In yet another embodiment the one or more microbially stabilizing compounds inhibit the activity of one or more bacteriostats disclosed herein. In still another embodiment the one or more microbially stabilizing compounds inhibit the activity of formaldhyde, benzyl-hemiformal (phenylmethoxymethanol), 2-bromo-2-nitro-1,3-propanadiol, 1-(3-chloroallyl)-3, 5,7-triaza-1-azoniaadamantane chloride, dibromonitrilopropionamide, 1,2-benzisothiazolin-3-one, 5-chloro-2-methyl-4-isothiazolin-3-one, 2-methyl-4-isothiazolin-3-one, diazolidinyl urea, tris(hydroxymethyl)nitromethane, sodium o-phenylphenate, copper arsenates, cuprous oxide, compounds of arsenic, copper, mercury, quaternary ammonium compounds, sodium azide, thimerosol, or combinations thereof.

In still another embodiment, the microbially stabilizing compound is yeast extract. Yeast extracts are widely used, e.g., for flavor in the food industries, in microorganism fermentation media, and as health foods. The production of yeast extract is described in literature, see e.g. Kelly, M. (1982) Yeast Extract (In: Industrial Enzymology, Godfrey, T. ed.) or Chae, H. J. et al. (2001), Bioresource Technology 76, 253-258. It is typically manufactured by breaking down the yeast by acid hydrolysis or mechanical or chemical disruption of the cells followed by autolysis with endogenous enzymes to degrade the macromolecular structures of the yeast, in particular the proteins, into the maximum amount of soluble material. Possibly, exogenous enzymes, including proteases such as papain, are added to augment the effect of the yeast's own enzymes. After the enzymatic hydrolysis, the yeast extract is separated from the cell debris and possibly pasteurized and concentrated.

In another embodiment, the microbially stabilizing compound is calcium caseinate.

In still another embodiment, the microbially stabilizing compound is a dairy substrate. In a particular embodiment, the microbially stabilizing compound is milk. Indeed, it is contemplated that milk in any form will be acceptable according to the embodiments disclosed herein. In some embodiments, cream obtained from any suitable milk finds use.

In still another embodiment, the microbially stabilizing compound is urea as well as isomers, salts, solvates, and derivatives thereof.

In still another embodiment, the microbially stabilizing compound is a hematinic agent.

In still another embodiment, the microbially stabilizing compound is beef extract. Beef extract is well known in the art.

In still another embodiment, the microbially stabilizing compound is ammonia as well as isomers, salts, solvates, and derivatives thereof.

In still another embodiment, the microbially stabilizing compound is an amino acid, an amino acid analog, an unnatural amino acid, an amino acid mimetic, or a combination thereof. Amino acids, as defined herein, may be referred to by either the commonly known three letter symbols or by the one-letter symbols recommended by the IUPAC-IUB Biochemical Nomenclature Commission. Nucleotides, likewise, may be referred to by their commonly accepted single-letter codes. In a particular embodiment, the amino acid is tryptophan.

In still another embodiment, the microbially stabilizing compound is one or more ammonium salts.

In still another embodiment, the microbially stabilizing compound is one or more ferric salts, ferrous salts, or combinations thereof.

In still another embodiment, the microbially stabilizing compound is gluconolactone as well as isomers, salts, and solvates thereof.

In still another embodiment the microbially stabilizing compound is glutathione as well as isomers, salts, and solvates thereof.

In still another embodiment, the microbially stabilizing compound is lecithin. In a particular embodiment, lecithin includes phosphatide mixtures commonly derived from eggs, fish, brewer's yeast, and vegetable sources, especially soy; however, any phosphatide mixture can be used in the present disclosure regardless of source. The four major components of such a phosphatide mixture are phosphatidylcholine, phosphatidylethanolamine, phosphatidylinositol, and phosphatidic acid. Lecithins have been referred to in some literature by the following names: PC-55, Ethanolamine, and Serine.

In still another embodiment, the microbially stabilizing compound is one or more polysorbates. Non-limiting examples of polysorbates include polysorbate 20 (poly(ethylene oxide) (20) sorbitan monolaurate, Tween 20) or polysorbate 80 (poly(ethylene oxide) (80) sorbitan monolaurate, Tween 80).

In still another embodiment, the microbially stabilizing compound is albumin. In some embodiments, the albumin is a mammalian albumin, or a variant or derivative thereof. Non-limiting examples of mammalian albumins that can be used include human, bovine, ovine, caprine, rabbit, feline, canine, porcine, primate, or rodent albumin.

In still another embodiment, the microbially stabilizing compound is a peptone. Non-limiting examples include tryptic or papain peptones that can be used include animal or plant derived tryptic peptones. In a particular embodiment, the digested peptone is from soy meal. In another embodiment, the peptone is a soy peptone (e.g., peptones derived from soy meal). In still another embodiment the soy peptone is tryptic soy broth.

In still another embodiment, the microbially stabilizing compound is selected from the group consisting of yeast extract, calcium caseinate, milk, urea, hematinic agents, beef extract, ammonia, amino acids, ammonium salts, ferric salts, ferrous salts, gluconolactone, glutathione, lecithin, polysorbates, albumin, soy peptones, and combinations thereof.

Carriers:

The compositions described herein may further comprise one or more carriers to deliver one or more actives described herein (e.g., microbially stabilizing compounds, or an agriculturally beneficial ingredient, e.g., beneficial microorganisms, etc.). Non-limiting examples of carriers described herein include liquids, gels, slurries, or solids (including wettable powders or dry powders). The selection of the carrier material will depend on the intended application. The carrier may, for example, be a soil-compatible carrier, a seed-compatible carrier and/or a foliar-compatible carrier. In a particular embodiment, the carrier is a seed-compatible carrier.

In one embodiment, the carrier is a liquid carrier. Non-limiting examples of liquids useful as carriers for the compositions disclosed herein include water, an aqueous solution, or a non-aqueous solution. In a particular embodiment the carrier is water.

If a liquid carrier is used, the liquid carrier may further include growth media to culture one or more microbial strains used in the compositions described. Non-limiting examples of suitable growth media for microbial strains include YEM media, mannitol yeast extract, glycerol yeast extract, Czapek-Dox medium, potato dextrose broth, or any media known to those skilled in the art to be compatible with, and/or provide growth nutrients to microbial strain which may be included to the compositions described herein.

Agriculturally Beneficial Ingredients:

The compositions disclosed herein may comprise one or more agriculturally beneficial ingredients. Non-limiting examples of agriculturally beneficial ingredients include one or more biologically active ingredients, nutrients, biostimulants, preservatives, polymers, wetting agents, surfactants, herbicides, fungicides, insecticides, or combinations thereof.

Biologically Active Ingredient(s):

The compositions described herein may optionally include one or more biologically active ingredients as described herein. Non-limiting examples of biologically active ingredients include plant signal molecules (e.g., lipo-chitooligosaccharides (LCO), chitooligosaccharides (CO), flavonoids, chitinous compounds, jasmonic acid or derivatives thereof, linoleic acid or derivatives thereof, linolenic acid or derivatives thereof, karrikins, etc.) and beneficial microorganisms (e.g., *Rhizobium* spp., *Bradyrhizobium* spp., *Sinorhizobium* spp., *Azorhizobium* spp., *Glomus* spp., *Gigaspora* spp., *Hymenoscyphous* spp., *Oidiodendron* spp., *Laccaria* spp., *Pisolithus* spp., *Rhizopogon* spp., *Scleroderma* spp., *Rhizoctonia* spp., *Acinetobacter* spp., *Arthrobacter* spp., *Arthrobotrys* spp., *Aspergillus* spp., *Azospirillum* spp, *Bacillus* spp, *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.).

Plant Signal Molecule(s):

In an embodiment, the compositions described herein may optionally include one or more plant signal molecules. In one embodiment, the one or more plant signal molecules are one or more LCOs. In another embodiment, the one or more plant signal molecules are one or more COs. In still another embodiment, the one or more plant signal molecules are one or more chitinous compounds. In another embodiment, the one or more plant signal molecules are one or more flavonoids. In yet another embodiment, the one or more plant signal molecules are one or more non-flavonoid nod gene inducers (e.g., jasmonic acid, linoleic acid, linolenic acid, and derivatives thereof). In still yet another embodiment, the one or more plant signal molecules are one or more karrikins or derivatives thereof. In still another embodiment, the one or more plant signal molecules are one or more LCOs, one or more COs, one or more chitinous compounds, one or more flavonoids, one or more non-flavonoid nod gene inducers and derivatives thereof, one or more karrikins and derivatives thereof, or any signal molecule combination thereof.

LCOs:

Lipo-chitooligosaccharide compounds (LCOs), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. LCOs are intended to include all LCOs as well as isomers, salts, and solvates thereof. An example of an LCO is presented below as formula I:

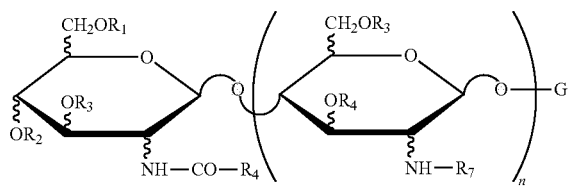

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_yCO-$ where x is an integer between 0 and 17, and y is an integer between 1 and 35, or any other acyl group such as for example a carbamyl, $R_4$ represents a mono-, di-, tri- and tetraunsaturated aliphatic chain containing at least 12 carbon atoms, and n is an integer between 1 and 4.

LCOs may be obtained (isolated and/or purified) from bacteria such as *Rhizobia*, e.g., *Rhizobium* spp., *Bradyrhizobium* spp., *Sinorhizobium* spp. and *Azorhizobium* spp. LCO structure is characteristic for each such bacterial species, and each strain may produce multiple LCO's with different structures. For example, specific LCOs from *S. meliloti* have also been described in U.S. Pat. No. 5,549,718 as having the formula II:

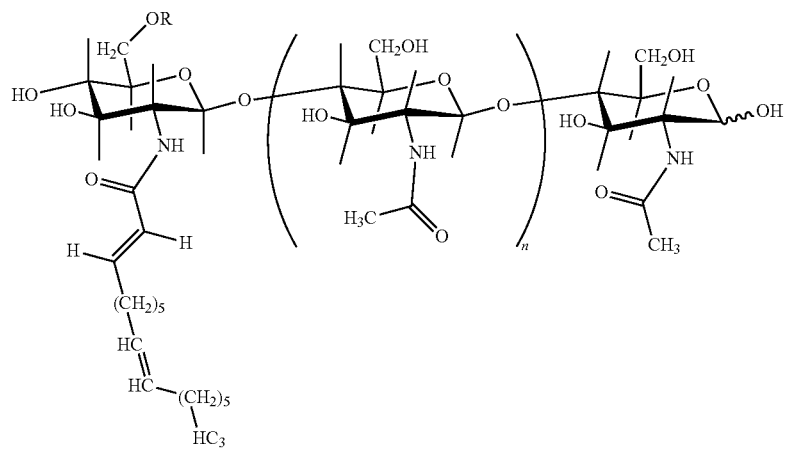

in which R represents H or CH$_3$CO— and n is equal to 2 or 3.

Even more specific LCOs include NodRM, NodRM-1, NodRM-3. When acetylated (the R=CH$_3$CO—), they become AcNodRM-1, and AcNodRM-3, respectively (U.S. Pat. No. 5,545,718).

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V (C$_{18:1}$); BjNod-V (A$_C$, C$_{18:1}$), BjNod-V (C$_{16:1}$); and BjNod-V (A$_C$, C$_{16:0}$), with "V" indicating the presence of five N-acetylglucosamines; "Ac" an acetylation; the number following the "C" indicating the number of carbons in the fatty acid side chain; and the number following the ":" the number of double bonds.

LCOs used in compositions of the disclosure may be obtained (i.e., isolated and/or purified) from bacterial strains that produce LCO's, such as strains of *Azorhizobium*, *Bradyrhizobium* (including *B. japonicum*), *Mesorhizobium*, *Rhizobium* (including *R. leguminosarum*), *Sinorhizobium* (including *S. meliloti*), and bacterial strains genetically engineered to produce LCO's.

Also encompassed by the present disclosure are compositions using LCOs obtained (i.e., isolated and/or purified) from a mycorrhizal fungus, such as fungi of the group Glomerocycota, e.g., *Glomus intraradicus*. The structures of representative LCOs obtained from these fungi are described in WO 2010/049751 (the LCOs described therein also referred to as "Myc factors").

Further encompassed by compositions of the present disclosure is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present disclosure) for the construction of LCOs may also be synthesized by genetically engineered organisms, e.g., as in Samain, et al., Carb. Res. 302:35-42 (1997); Samain, et al., J. Biotechnol. 72:33-47 (1999).

LCO's may be utilized in various forms of purity and may be used alone or in the form of a culture of LCO-producing bacteria or fungi. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

COs:

Chitooligosaccharides (COs) are known in the art as β-1-4 linked N actyl glucosamine structures identified as chitin oligomers, also as N-acetylchitooligosaccharides. CO's have unique and different side chain decorations which make them different from chitin molecules [(C$_8$H$_{13}$NO$_5$)n, CAS No. 1398-61-4], and chitosan molecules [(C$_5$H$_{11}$NO$_4$) n, CAS No. 9012-76-4]. Representative literature describing the structure and production of COs is as follows: Van der Holst, et al., Current Opinion in Structural Biology, 11:608-616 (2001); Robina, et al., Tetrahedron 58:521-530 (2002); Hanel, et al., Planta 232:787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999). The COs may be synthetic or recombinant. Methods for preparation of recombinant COs are known in the art. See, e.g., Samain, et al. (supra.); Cottaz, et al., Meth. Eng. 7(4):311-7 (2005) and Samain, et al., J. Biotechnol. 72:33-47 (1999). COs are intended to include isomers, salts, and solvates thereof.

Chitinous Compounds:

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl] methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan, (IUPAC: 5-amino-6-[5-amino-6-[5-amino-4,6-dihydroxy-2(hydroxymethyl)oxan-3-yl]oxy-4-hydroxy-2-(hydroxymethyl) oxan-3-yl]oxy-2(hydroxymethyl)oxane-3,4-diol), and isomers, salts, and solvates thereof.

These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids:

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include are known in the art. See, Jain, et al., J. Plant Biochem. & Biotechnol. 11:1-10 (2002); Shaw, et al., Environmental Microbiol. 11:1867-80 (2006). Flavonoid compounds are commercially available, e.g., from Novozymes BioAg, Saskatoon, Canada; Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005). Flavonoid compounds are intended to include all flavonoid compounds as well as isomers, salts, and solvates thereof.

The one or more flavonoids may be a natural flavonoid (i.e., not synthetically produced), a synthetic flavonoid (e.g., a chemically synthesized flavonoid) or a combination thereof. In a particular embodiment, the compositions described herein comprise a flavanol, a flavone, an anthocyanidin, an isoflavonoid, a neoflavonoid and combinations thereof, including all isomer, solvate, hydrate, polymorphic, crystalline form, non-crystalline form, and salt variations thereof.

In an embodiment, the compositions described herein may comprise one or more flavanols. In still another embodiment, the compositions described herein may comprise one or more flavanols selected from the group consisting of flavan-3-ols (e.g., catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), etc.), flavan-4-ols, flavan-3,4-diols (e.g., leucoanthocyanidin), proanthocyanidins (e.g., includes dimers, trimer, oligomers, or polymers of flavanols), and combinations thereof. In still yet another embodiment, the compositions described herein may comprise one or more flavanols selected from the group consisting of catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), flavan-4-ol, leucoanthocyanidin, and dimers, trimers, oligomers or polymers thereof.

In another embodiment, the compositions described herein may comprise one or more flavones. In still another embodiment, the compositions described herein may comprise one or more flavones selected from the group consisting of flavones (e.g., luteolin, apigenin, tangeritin, etc.), flavonols (e.g., quercetin, quercitrin, rutin, kaempferol, kaempferitrin, astragalin, sophoraflavonoloside, myricetin, fisetin, isorhamnetin, pachypodol, rhamnazin, etc.), flavanones (e.g. hesperetin, hesperidin, naringenin, eriodictyol, homoeriodictyol, etc.), and flavanonols (e.g., dihydroquercetin, dihydrokaempferol, etc.). In still yet another embodiment, the compositions described herein may comprise one or more flavones selected from the group consisting of luteolin, apigenin, tangeritin, quercetin, quercitrin, rutin, kaempferol, kaempferitrin, astragalin, sophoraflavonoloside, myricetin, fisetin, isorhamnetin, pachypodol, rhamnazin, hesperetin, hesperidin, naringenin, eriodictyol, homoeriodictyol, dihydroquercetin, dihydrokaempferol, and combinations thereof.

In still another embodiment, the compositions described herein may comprise one or more anthocyanidins. In yet another embodiment, the compositions described herein may comprise one or more anthocyanidins selected from the group selected from the group consisting of cyanidins, delphinidins, malvidins, pelargonidins, peonidins, petunidins, and combinations thereof.

In another embodiment, the compositions described herein may comprise one or more isoflavonoids. In still yet another embodiment, the compositions described herein comprise one or more isoflavonoids selected from the group consisting of phytoestrogens, isoflavones (e.g., genistein, daidzein, glycitein, etc.), and isoflavanes (e.g., equol, lonchocarpane, laxiflorane, etc.), and combinations thereof. In yet another embodiment the compositions described herein may comprise one or more isoflavonoids selected from the group consisting of genistein, daidzein, glycitein, equol, lonchocarpane, laxiflorane, and combinations thereof.

In another embodiment, the compositions described herein may comprise one or more neoflavonoids. In yet another embodiment, the compositions described herein may comprise one or more neoflavonoids selected from the group consisting of neoflavones (e.g., calophyllolide), neoflavenes (e.g., dalbergichromene), coutareagenins, dalbergins, nivetins, and combinations thereof. In still yet another embodiment, the compositions described herein may comprise one or more neoflavonoids selected from the group consisting of calophyllolide, dalbergichromene, coutareagenin, dalbergin, nivetin, and combinations thereof.

In another embodiment, the compositions described herein may comprise one or flavonoids selected from the group consisting of catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), flavan-4-ol, leucoanthocyanidin, proanthocyanidins, luteolin, apigenin, tangeritin, quercetin, quercitrin, rutin, kaempferol, kaempferitrin, astragalin, sophoraflavonoloside, myricetin, fisetin, isorhamnetin, pachypodol, rhamnazin, hesperetin, hesperidin, naringenin, eriodictyol, homoeriodictyol, dihydroquercetin, dihydrokaempferol, cyanidins, delphinidins, malvidins, pelargonidins, peonidins, petunidins, genistein, daidzein, glycitein, equol, lonchocarpane, laxiflorane, calophyllolide, dalbergichromene, coutareagenin, dalbergin, nivetin, and combinations thereof. In still another embodiment, the compositions described herein may comprise one or more flavonoids selected from the group consisting of hesperetin, hesperidin, naringenin, genistein, daidzein, and combinations thereof. In a particular embodiment, the composition described herein may comprise the flavonoid hesperetin. In another particular embodiment, the composition described herein may comprise the flavonoid hesperidin. In still another particular embodiment, the composition described herein may comprise the flavonoid naringenin. In still yet another particular embodiment, the composition described herein may comprise the flavonoid genistein. In yet still another particular embodiment, the composition described herein may comprise the flavonoid daidzein.

Non-Flavonoid Nod-Gene Inducer(s):

Jasmonic acid (JA, [1R-[1α,2β(Z)]]-3-oxo-2-(pentenyl) cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, may also be used in the compositions described herein. Non-flavonoid nod-gene inducers are intended to include not only the non-flavonoid nod-gene inducers described herein, but isomers, salts, and solvates thereof.

Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibberella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linoleic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in compositions of the present disclosure include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a C$_1$-C$_8$ unbranched or branched alkyl group, e.g., a methyl, ethyl or propyl group; an alkenyl group, such as a C$_2$-C$_8$ unbranched or branched alkenyl group; an alkynyl group, such as a C$_2$-C$_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a C$_1$-C$_8$ unbranched or branched alkyl group, e.g., a methyl, ethyl or propyl group; an alkenyl group, such as a C$_2$-C$_8$ unbranched or branched alkenyl group; an alkynyl group, such as a C$_2$-C$_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikin(s):

Karrikins are vinylogous 4H-pyrones e.g., 2H-furo[2,3-c]pyran-2-ones including derivatives and analogues thereof. It is intended that the karrikins include isomers, salts, and solvates thereof. Examples of these compounds are represented by the following structure:

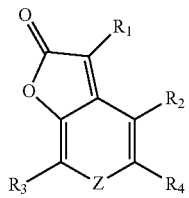

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$, and R$_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present disclosure include the following: 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H), 3,6-dimethylfuro[2,3-c]pyridin-2(6H)-one (where Z=N—CH$_3$, R$_1$=CH$_3$, R$_2$, R$_3$, R$_4$=H). See, U.S. Pat. No. 7,576,213. These molecules are also known as karrikins. See, Halford, "Smoke Signals," in Chem. Eng. News (Apr. 12, 2010), at pages 37-38 (reporting that karrikins or butenolides which are contained in smoke act as growth stimulants and spur seed germination after a forest fire, and can invigorate seeds such as corn, tomatoes, lettuce and onions that had been stored). These molecules are the subject of U.S. Pat. No. 7,576,213.

Beneficial Microorganism(s):

In an embodiment, the compositions described herein may optionally include one or more beneficial microorganisms. The one or more beneficial microorganisms may be in a spore form, a vegetative form, or a combination thereof. The one or more beneficial microorganisms may include any number of microorganisms having one or more beneficial properties (e.g., produce one or more of the plant signal molecules described herein, enhance nutrient and water uptake, promote and/or enhance nitrogen fixation, enhance growth, enhance seed germination, enhance seedling emergence, break the dormancy or quiescence of a plant, provide anti-fungal activity, etc.).

In one embodiment, the one or more beneficial microorganisms are diazotrophs (i.e., bacteria which are symbiotic nitrogen-fixing bacteria). In still another embodiment, the one or more beneficial microorganisms are bacterial diazotrophs selected from the genera *Rhizobium* spp., *Bradyrhizobium* spp., *Azorhizobium* spp., *Sinorhizobium* spp., *Mesorhizobium* spp., *Azospirillum* spp., and combinations thereof. In still another embodiment, the one or more beneficial microorganisms are bacteria selected from the group consisting of *Rhizobium cellulosilyticum, Rhizobium daejeonense, Rhizobium etli, Rhizobium galegae, Rhizobium gallicum, Rhizobium giardinii, Rhizobium hainanense, Rhizobium huautlense, Rhizobium indigoferae, Rhizobium leguminosarum, Rhizobium loessense, Rhizobium lupini, Rhizobium lusitanum, Rhizobium meliloti, Rhizobium mongolense, Rhizobium miluonense, Rhizobium sullae, Rhizobium tropici, Rhizobium undicola, Rhizobium yanglingense, Bradyrhizobium bete, Bradyrhizobium canariense, Bradyrhizobium elkanii, Bradyrhizobium iriomotense, Bradyrhizobium japonicum, Bradyrhizobium jicamae, Bradyrhizobium liaoningense, Bradyrhizobium pachyrhizi, Bradyrhizobium yuanmingense, Azorhizobium caulinodans, Azorhizobium doebereinerae, Sinorhizobium abri, Sinorhizobium adhaerens, Sinorhizobium americanum, Sinorhizobium aboris Sinorhizobium fredii, Sinorhizobium* indiaense, Sinorhizobium kostiense, Sinorhizobium kummerowiae, Sinorhizobium medicae, Sinorhizobium meliloti, Sinorhizobium mexicanus, Sinorhizobium morelense, Sinorhizobium saheli, Sinorhizobium terangae, Sinorhizobium xinjiangense, Mesorhizobium albiziae, Mesorhizobium amorphae, Mesorhizobium chacoense, Mesorhizobium ciceri, Mesorhizobium huakuii, Mesorhizobium loti, Mesorhizobium mediterraneum, Mesorhizobium pluifarium, Mesorhizobium septentrionale, Mesorhizobium temperatum, Mesorhizobium tianshanense, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae, and combinations thereof.

In a particular embodiment, the beneficial microorganism is a bacterial daizotroph selected from the group consisting of Bradyrhizobium japonicum, Rhizobium leguminosarum, Rhizobium meliloti, Sinorhizobium meliloti, Azospirillum brasilense, and combinations thereof. In another embodiment, the beneficial microorganism is the bacterial daizotroph Bradyrhizobium japonicum. In another embodiment, the beneficial microorganism is the bacterial daizotroph Rhizobium leguminosarum. In another embodiment, the beneficial microorganism is the bacterial daizotroph Rhizobium meliloti. In another embodiment, the beneficial microorganism is the bacterial daizotroph Sinorhizobium meliloti. In another embodiment, the beneficial microorganism is the bacterial daizotroph Azospirillum brasilense.

In a particular embodiment, the one or more diazotrophs comprises one or more strains of Rhizobium leguminosarum. In another particular embodiment, the strain of R. leguminosarum comprises the strain SO12A-2-(IDAC 080305-01). In another particular embodiment, the one or more diazotrophs comprises a strain of Bradyrhizobium japonicum. In still another particular embodiment, the strain of Bradyrhizobium japonicum comprises the strain B. japonicum USDA 532C, B. japonicum USDA 110, B. japonicum USDA 123, B. japonicum USDA 127, B. japonicum USDA 129, B. japonicum NRRL B-50608, B. japonicum NRRL B-50609, B. japonicum NRRL B-50610, B. japonicum NRRL B-50611, B. japonicum NRRL B-50612, B. japonicum NRRL B-50592 (deposited also as NRRL B-59571), B. japonicum NRRL B-50593 (deposited also as NRRL B-59572), B. japonicum NRRL B-50586 (deposited also as NRRL B-59565), B. japonicum NRRL B-50588 (deposited also as NRRL B-59567), B. japonicum NRRL B-50587 (deposited also as NRRL B-59566), B. japonicum NRRL B-50589 (deposited also as NRRL B-59568), B. japonicum NRRL B-50591 (deposited also as NRRL B-59570), B. japonicum NRRL B-50590 (deposited also as NRRL B-59569), NRRL B-50594 (deposited also as NRRL B-50493), B. japonicum NRRL B-50726, B. japonicum NRRL B-50727, B. japonicum NRRL B-50728, B. japonicum NRRL B-50729, B. japonicum NRRL B-50730, and combinations thereof.

In still yet a more particular embodiment, the one or more diazotrophs comprises one or more strains of R. leguminosarum comprises the strain SO12A-2-(IDAC 080305-01), B. japonicum USDA 532C, B. japonicum USDA 110, B. japonicum USDA 123, B. japonicum USDA 127, B. japonicum USDA 129, B. japonicum NRRL B-50609, B. japonicum NRRL B-50610, B. japonicum NRRL B-50611, B. japonicum NRRL B-50612, B. japonicum NRRL B-50592 (deposited also as NRRL B-59571), B. japonicum NRRL B-50593 (deposited also as NRRL B-59572), B. japonicum NRRL B-50586 (deposited also as NRRL B-59565), B. japonicum NRRL B-50588 (deposited also as NRRL B-59567), B. japonicum NRRL B-50587 (deposited also as NRRL B-59566), B. japonicum NRRL B-50589 (deposited also as NRRL B-59568), B. japonicum NRRL B-50591 (deposited also as NRRL B-59570), B. japonicum NRRL B-50590 (deposited also as NRRL B-59569), NRRL B-50594 (deposited also as NRRL B-50493), B. japonicum NRRL B-50726, B. japonicum NRRL B-50727, B. japonicum NRRL B-50728, B. japonicum NRRL B-50729, B. japonicum NRRL B-50730, and combinations thereof.

In another embodiment, the one or more beneficial microorganisms comprise one or more phosphate solubilizing microorganisms. Phosphate solubilizing microorganisms include fungal and bacterial strains. In an embodiment, the phosphate solubilizing microorganism are microorganisms selected from the genera consisting of Acinetobacter spp., Arthrobacter spp, Arthrobotrys spp., Aspergillus spp., Azospirillum spp., Bacillus spp., Burkholderia spp., Candida spp., Chryseomonas spp., Enterobacter spp., Eupenicillium spp., Exiguobacterium spp., Klebsiella spp., Kluyvera spp., Microbacterium spp., Mucor spp., Paecilomyces spp., Paenibacillus spp., Penicillium spp., Pseudomonas spp., Serratia spp., Stenotrophomonas spp., Streptomyces spp., Streptosporangium spp., Swaminathania spp., Thiobacillus spp., Torulospora spp., Vibrio spp., Xanthobacter spp., Xanthomonas spp., and combinations thereof. In still yet another embodiment, the phosphate solubilizing microorganism is a microorganism selected from the group consisting of Acinetobacter calcoaceticus, Arthrobotrys oligospora, Aspergillus niger, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter taylorae, Eupenicillium parvum, Kluyvera cryocrescens, Mucor ramosissimus, Paecilomyces hepialid, Paecilomyces marquandii, Paenibacillus macerans, Paenibacillus mucilaginosus, Penicillium bilaiae (formerly known as Penicillium bilaii), Penicillium albidum, Penicillium aurantiogriseum, Penicillium chrysogenum, Penicillium citreonigrum, Penicillium citrinum, Penicillium digitatum, Penicillium frequentas, Penicillium fuscum, Penicillium gaestrivorus, Penicillium glabrum, Penicillium griseofulvum, Penicillium implicatum, Penicillium janthinellum, Penicillium lilacinum, Penicillium minioluteum, Penicillium montanense, Penicillium nigricans, Penicillium oxalicum, Penicillium pinetorum, Penicillium pinophilum, Penicillium purpurogenum, Penicillium radicans, Penicillium radicum, Penicillium raistrickii, Penicillium rugulosum, Penicillium simplicissimum, Penicillium solitum, Penicillium variabile, Penicillium velutinum, Penicillium viridicatum, Penicillium glaucum, Penicillium fussiporus, and Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Swaminathania salitolerans, Thiobacillus ferrooxidans, Torulospora

*globosa, Vibrio proteolyticus, Xanthobacter agilis, Xanthomonas campestris,* and combinations thereof.

In a particular embodiment, the one or more phosphate solubilizing microorganisms is a strain of the fungus *Penicillium*. In another embodiment, the one or more *Penicillium* species is *P. bilaiae, P. gaestrivorus,* or combinations thereof.

In a particular embodiment, the one or more phosphate solubilizing microorganisms is a strain of the fungus *Penicillium*. In another embodiment, the one or more *Penicillium* species is *P. bilaiae, P. gaestrivorus,* or combinations thereof. In a particular embodiment, the strain of *Penicillium* comprises *P. bilaiae* NRRL 50169, *P. bilaiae* ATCC 20851, *P. bilaiae* ATCC 22348, *P. bilaiae* ATCC 18309, *P. bilaiae* NRRL 50162 and combinations thereof. In another particular embodiment, the strain of *Penicillium* comprises strain *P. gaestrivorus* NRRL 50170. In still yet another particular embodiment, the strain of *Penicillium* comprises *P. bilaiae* NRRL 50169, *P. bilaiae* ATCC 20851, *P. bilaiae* ATCC 22348, *P. bilaiae* ATCC 18309, *P. bilaiae* NRRL 50162, *P. gaestrivorus* NRRL 50170, and combinations thereof.

In another embodiment the beneficial microorganism is one or more mycorrhiza. In particular, the one or more mycorrhiza is an endomycorrhiza (also called vesicular arbuscular mycorrhizas, VAMs, arbuscular mycorrhizas, or AMs), an ectomycorrhiza, or a combination thereof.

In one embodiment, the one or more mycorrhiza is an endomycorrhiza of the phylum Glomeromycota and genera *Glomus* and *Gigaspora*. In still a further embodiment, the endomycorrhiza is a strain of *Glomus aggregatum, Glomus brasilianum, Glomus clarum, Glomus deserticola, Glomus etunicatum, Glomus fasciculatum, Glomus intraradices, Glomus monosporum,* or *Glomus mosseae, Gigaspora margarita,* or a combination thereof.

In another embodiment, the one or more mycorrhiza is an ectomycorrhiza of the phylum Basidiomycota, Ascomycota, and Zygomycota. In still yet another embodiment, the ectomycorrhiza is a strain of *Laccaria bicolor, Laccaria laccata, Pisolithus tinctorius, Rhizopogon amylopogon, Rhizopogon fulvigleba, Rhizopogon luteolus, Rhizopogon villosuli, Scleroderma cepa, Scleroderma citrinum,* or a combination thereof.

In still another embodiment, the one or more mycorrhiza is an ecroid mycorrhiza, an arbutoid mycorrhiza, or a monotropoid mycorrhiza. Arbuscular and ectomycorrhizas form ericoid mycorrhiza with many plants belonging to the order Ericales, while some Ericales form arbutoid and monotropoid mycorrhizas. All orchids are mycoheterotrophic at some stage during their lifecycle and form orchid mycorrhizas with a range of basidiomycete fungi. In one embodiment, the mycorrhiza may be an ericoid mycorrhiza, preferably of the phylum Ascomycota, such as *Hymenoscyphous ericae* or *Oidiodendron sp.* In another embodiment, the mycorrhiza also may be an arbutoid mycorrhiza, preferably of the phylum Basidiomycota. In yet another embodiment, the mycorrhiza may be a monotripoid mycorrhiza, preferably of the phylum Basidiomycota. In still yet another embodiment, the mycorrhiza may be an orchid mycorrhiza, preferably of the genus *Rhizoctonia*.

In still another embodiment, the one or more beneficial microorganisms are fungicides, i.e., have fungicidal activity, (e.g., biofungicides). Non-limiting examples of biofungicides are provided below in the "Fungicides" section.

Fungicide(s):

In one embodiment, the compositions described herein may further comprise one or more fungicides. Fungicides useful to the compositions described herein may be biological fungicides, chemical fungicides, or combinations thereof. Fungicides may be selected so as to be provide effective control against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). More common fungal pathogens that may be effectively targeted include *Pytophthora, Rhizoctonia, Fusarium, Pythium, Phomopsis* or *Selerotinia* and *Phakopsora* and combinations thereof.

In certain embodiments, the biological fungicide can be a bacterium of the genus *Actinomycetes, Agrobacterium, Arthrobacter, Alcaligenes, Aureobacterium, Azobacter, Bacillus, Beijerinckia, Brevibacillus, Burkholderia, Chromobacterium, Clostridium, Clavibacter, Comomonas, Corynebacterium, Curtobacterium, Enterobacter, Flavobacterium, Gluconobacter, Hydrogenophage, Klebsiella, Methylobacterium, Paenibacillus, Pasteuria, Phingobacterium, Photorhabdus, Phyllobacterium, Pseudomonas, Rhizobium, Serratia, Stenotrophomonas, Variovorax,* and *Xenorhadbus.* In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage,* and *Pseudomona fluorescens.*

In certain embodiments the biological fungicide can be a fungus of the genus *Alternaria, Ampelomyces, Aspergillus, Aureobasidium, Beauveria, Colletotrichum, Coniothyrium, Gliocladium, Metarhizium, Muscodor, Paecilonyces, Trichoderma, Typhula, Ulocladium,* and *Verticilium.* In particular embodiments the fungus is *Beauveria bassiana, Coniothyrium minitans, Gliocladium virens, Metarhizium anisopliae, Muscodor albus, Paecilomyces lilacinus,* or *Trichoderma polysporum.*

Non-limiting examples of biological fungicides that may be suitable for use in the present disclosure include *Ampelomyces quisqualis* (e.g., AQ 10® from Intrachem Bio GmbH & Co. KG, Germany), *Aspergillus flavus* (e.g., AFLA-GUARD® from Syngenta, CH), *Aureobasidium pullulans* (e.g., BOTECTOR® from bio-ferm GmbH, Germany), *Bacillus pumilus* (e.g., isolate NRRL-Nr. B-21661 in RHAPSODY®, SERENADE® MAX and SERENADE® ASO from Fa. AgraQuest Inc., USA), *Bacillus amyloliquefaciens, Bacillus amyloliquefaciens* FZB24 (e.g., TAEGRO® from Novozymes Biologicals, Inc., USA), *Bacillus amyloliquefaciens* TJ1000 (e.g., also known as 1BE, isolate ATCC BAA-390), *Candida oleophila, Candida oleophila* 1-82 (e.g., ASPIRE® from Ecogen Inc., USA), *Candida saitoana* (e.g., BIOCURE® (in mixture with lysozyme) and BIOCOAT® from Micro Flo Company, USA (BASF SE) and Arysta), *Clonostachys rosea* f. *catenulata,* also named *Gliocladium catenulatum* (e.g., isolate J1446: PRESTOP® from Verdera, Finland), *Coniothyrium minitans* (e.g., CONTANS® from Prophyta, Germany), *Cryphonectria parasitica* (e.g., *Endothia parasitica* from CNICM, France), *Cryptococcus albidus* (e.g., YIELD PLUS® from Anchor Bio-Technologies, South Africa), *Fusarium oxysporum* (e.g., BIOFOX® from S.I.A.P.A., Italy, FUSACLEAN® from Natural Plant Protection, France), *Metschnikowia fructicola* (e.g., SHEMER® from Agrogreen, Israel), *Microdochium dimerum* (e.g., ANTIBOT® from Agrauxine, France), *Phlebiopsis gigantea* (e.g., ROTSOP® from Verdera, Finland), *Pseudozyma flocculosa* (e.g., SPORODEX® from Plant Products Co. Ltd., Canada), *Pythium oligandrum, Pythium oligandrum* DV74 (e.g., POLYVERSUM® from Remeslo SSRO, Biopreparaty, Czech Rep.), *Reynoutria sachlinensis* (e.g., REGALIA® from Marrone BioInnovations, USA), *Talaromyces flavus, Talaromyces flavus* V117b (e.g., PROTUS® from Prophyta, Germany), *Trichoderma asperellum, Trichoderma asperellum* SKT-1 (e.g., ECO-HOPE® from Kumiai Chemical Industry Co., Ltd., Japan), *Trichoderma atroviride, Trichoderma atroviride* LC52 (e.g., SENTINEL® from Agrimm Technologies Ltd, NZ), *Trichoderma harzianum, Trichoderma harzianum* T-22 (e.g., PLANTSHIELD® der Firma BioWorks Inc., USA), *Trichoderma harzianum* TH 35 (e.g., ROOT PRO® from Mycontrol Ltd., Israel), *Trichoderma harzianum* T-39 (e.g., TRICHODEX® and TRICHODERMA 2000® from Mycontrol Ltd., Israel and Makhteshim Ltd., Israel), *T. harzianum* ICC012, *T. harzianum* and *T. viride* (e.g., TRICHOPEL from Agrimm Technologies Ltd, NZ), *T. harzianum* ICC012 and *T. viride* ICC080 (e.g., REMEDIER® from Isagro Ricerca, Italy), *T. polysporum* and *T. harzianum* (e.g., BINAB® from BINAB Bio-Innovation AB, Sweden), *Trichoderma stromaticum* (e.g., TRICOVAB® from C.E.P.L.A.C., Brazil), *Trichoderma virens, T. virens* GL-21 (e.g., SOILGARD® from Certis LLC, USA), *T. virens* G1-3 (e.g., ATCC 58678, from Novozymes BioAg, Inc.), *T. virens* G1-21 (e.g., commercially available from Thermo Trilogy Corporation) *Trichoderma viride* (e.g., TRIECO® from Ecosense Labs. (India) Pvt. Ltd., Indien, BIO-CURE® F from T. Stanes & Co. Ltd., Indien), *T. viride* TV1 (e.g., *T. viride* TV1 from Agribiotec srl, Italy), *T. viride* ICC080, *Streptomyces lydicus, Streptomyces lydicus* WYEC 108 (e.g., isolate ATCC 55445 in ACTINOVATE®, ACTINO-VATE AG®, ACTINOVATE STP®, ACTINO-IRON®, ACTINOVATE L&G®, and ACTINOGROW® from Idaho Research Foundation, USA), *Streptomyces violaceusniger, Streptomyces violaceusniger* YCED 9 (e.g., isolate ATCC 55660 in DE-THATCH-9®, DECOMP-9®, and THATCH CONTROL® from Idaho Research Foundation, USA), *Streptomyces* WYE 53 (e.g., isolate ATCC 55750 in DE-THATCH-9®, DECOMP-9®, and THATCH CONTROL® from Idaho Research Foundation, USA) and *Ulocladium oudemansii, Ulocladium oudemansii* HRU3 (e.g., BOTRY-ZEN® from Botry-Zen Ltd, NZ).

In a particular embodiment, the biofungicide is *Bacillus amyloliquefaciens* FZB24. In another particular embodiment, the biofungicide is *Bacillus amyloliquefaciens* TJ1000. In yet another particular embodiment, the biofungicide is *Streptomyces lydicus* WYEC 108. In still yet another particular embodiment, the biofungicide is *Streptomyces violaceusniger* YCED 9. In another particular embodiment, the biofungicide is *Streptomyces* WYE 53. In yet another particular embodiment, the biofungicide is *Trichoderma virens* G1-3. In another particular embodiment, the biofungicide is *Trichoderma virens* G1-21.

In still another particular embodiment, the biofungicide is a combination of *Bacillus amyloliquefaciens* FZB24, *Bacillus amyloliquefaciens* TJ1000, *Streptomyces lydicus* WYEC 108, *Streptomyces violaceusniger* YCED 9, *Streptomyces* WYE 53, *Trichoderma virens* G1-3, *Trichoderma virens* G1-21, or combinations thereof (e.g., at least one, at least two, at least three, at least four, at least five, at least six, at least seven, up to and including all of the strains in combination).

In further embodiments the biological fungicide can be plant growth activators or plant defense agents including, but not limited to harpin, *Reynoutria sachalinensis*, etc.

Representative examples of useful chemical fungicides that may be suitable for use in the present disclosure include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles:

A) Strobilurins:
azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide;

B) Carboxamides:
carboxanilides: benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyrazole-4-carboxamide and N-(2-(1,3,3-trimethylbutyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide;

other carboxamides: carpropamid, dicyclomet, mandipropamid, oxytetracyclin, silthiofam and N-(6-methoxy-pyridin-3-yl)cyclopropanecarboxylic acid amide;

C) Azoles:
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, pefurazoate, prochloraz, triflumizol;

D) Heterocyclic Compounds:
pyridines: fluazinam, pyrifenox, 3-[5-(4-chloro-phenyl)-2,3-dimethyl-isoxazolidin-3-yl]-pyridine, 3-[5-(4-methylphenyl)-2,3-dimethyl-isoxazolidin-3-yl]-pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine;

E) Benzamidazoles:
carbendazim.

F) Other Active Substances:
guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dicloran, dinobuton, dinocap, nitrothal-isopropyl, tecnazen, organometal compounds: fentin salts, such as fentinacetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorus acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate and sulfur.

Commercial fungicides are most suitably used in accordance with the manufacturer's instructions at the recommended concentrations.

Herbicide(s):

In one embodiment, the compositions described herein may further comprise one or more herbicides. Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins. In a particular embodiment, the herbicide may be a pre-emergent herbicide, a post-emergent herbicide, or a combination thereof.

Suitable herbicides include chemical herbicides, natural herbicides (e.g., bioherbicides, organic herbicides, etc.), or combinations thereof. Non-limiting examples of suitable herbicides include acetochlor, dicamba, bentazon, acifluorfen, chlorimuron, lactofen, clomazone, fluazifop, flumioxazin, glufosinate, glyphosate, sethoxydim, imazethapyr, imazamox, fomesafe, fomesafen, flumiclorac, imazaquin, mesotrione, quizalofop, saflufenacil, sulcotrione, 2,4-dichlorophenoxyacetic acid (2,4-D), 2,4,5-trichlorophenoxyacetic acid (2,4,5-T), thaxtomin (e.g., the thaxtomins as described in U.S. Pat. No. 7,989,393) and clethodim. Commercial products containing each of these compounds are readily available. Herbicide concentration in the composition will generally correspond to the labeled use rate for a particular herbicide.

Insecticide(s), Acaricide(s) Nematicide(s):

In one embodiment, the compositions described herein may further comprise one or more insecticides, acaricides, nematicides, or combinations thereof. Insecticides useful to the compositions described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof. The insecticides, acaricides, and nematicides described herein may be chemical or natural (e.g., biological solutions, such as fungal pesticides, etc.).

Non-limiting examples of insecticides, acaricides, and nematicides that may be useful to the compositions disclosed herein include carbamates, diamides, macrocyclic lactones, neonicotinoids, organophosphates, phenylpyrazoles, pyrethrins, spinosyns, synthetic pyrethroids, tetronic and tetramic acids.

In particular embodiments insecticides, acaricides, and nematicides include acrinathrin, alpha-cypermethrin, beta-cyfluthrin, cyhalothrin, cypermethrin, deltamethrin csfenvalcrate, etofenprox, fenpropathrin, fenvalerate, flucythrinat, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (Rynaxypyr), chlothianidin, Cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole, and also products based on *Bacillus firmus* (I-1582, BioNeem, Votivo), and combinations thereof.

In a particular embodiment, the insecticide is a microbial insecticide. In a more particular embodiment, the microbial insecticide is a fungal insecticide. Non-limiting examples of fungal insecticides that may be used in the compositions disclosed herein are described in McCoy, C. W., Samson, R. A., and Coucias, D. G. "Entomogenous fungi. In "CRC Handbook of Natural Pesticides. Microbial Pesticides, Part A. Entomogenous Protozoa and Fungi." (C. M. Inoffo, ed.), (1988): Vol. 5, 151-236; Samson, R. A., Evans, H. C., and Latge', J. P. "Atlas of Entomopathogenic Fungi." (Springer-Verlag, Berlin) (1988); and deFaria, M. R. and Wraight, S. P. "Mycoinsecticides and Mycoacaricides: A comprehensive list with worldwide coverage and international classification of formulation types." Biol. Control (2007), doi: 10.1016/j.biocontrol.2007.08.001.

In one embodiment, non-limiting examples fungal insecticides that may be used in the compositions disclosed herein include species of *Coelomycidium, Myiophagus, Coelemomyces, Lagenidium, Leptolegnia, Couchia, Sporodiniella, Conidiobolus, Entomophaga, Entomophthora, Erynia, Massospora, Meristacrum, Neozygites, Pandora, Zoophthora, Blastodendrion, Metschnikowia, Mycoderma, Ascophaera, Cordyceps, Torrubiella, Nectria, Hypocrella, Calonectria, Filariomyces, Hesperomyces, Trenomyces, Myriangium, Podonectria, Akanthomyces, Aschersonia, Aspergillus,*

*Beauveria, Culicinomyces, Engyodontium, Fusarium, Gibellula, Hirsutella, Hymenostilbe, Isaria, Metarhizium, Nomuraea, Paecilomyces, Paraisaria, Pleurodesmospora, Polycephalomyces, Pseudogibellula, Sorosporella, Stillbella, Tetranacrium, Tilachlidium, Tolypocladium, Verticillium, Aegerita, Filobasidiella, Septobasidium, Uredinella,* and combinations thereof.

Non-limiting examples of particular species that may be useful as a fungal insecticide in the compositions described herein include *Trichoderma hamatum, Trichoderma hazarium, Alternaria cassiae, Fusarium lateritum, Fusarium solani, Lecanicillium lecanii, Aspergillus parasiticus, Verticillium lecanii, Metarhizium anisopliae,* and *Beauveria bassiana*. In an embodiment, the compositions disclosed herein may include any of the fungal insecticides provided above, including any combination thereof.

In one embodiment, the composition comprises at least one fungal insecticide from the genus *Metarhizium* spp., such as, *Metarhizium anisopliae* (also may be referred to in the art as *Metarrhizium anisopliae, Metarhizium brunneum,* or "green muscadine"). In at least one embodiment, the fungal insecticide comprises the strain *Metarhizium anisopliae*. In another embodiment, the composition comprises spores of the strain *Metarhizium anisopliae*.

In a particular embodiment, the composition comprises at least one fungal pesticide comprising *Metarhizium anisopliae* strain F52 (also known as *Metarhizium anisopliae* strain 52, *Metarhizium anisopliae* strain 7, *Metarhizium anisopliae* strain 43, *Metarhizium anisopliae* BIO-1020, TAE-001 and deposited as DSM 3884, DSM 3885, ATCC 90448, SD 170, and ARSEF 7711) (available from Novozymes Biologicals, Inc., USA). In still another particular embodiment, the composition comprises at least one fungal insecticide comprising spores of *Metarhizium anisopliae* strain F52.

In yet another embodiment the composition may further comprise at least one fungal insecticide from the genus *Beauveria* spp., such as, for example, *Beauveria bassiana*. In at least one embodiment, the fungal insecticide further comprises the strain *Beauveria bassiana*. In another embodiment, the composition further comprises spores of the strain *Beauveria bassiana*.

In a particular embodiment, the composition further comprises at least one fungal insecticide comprising *Beauveria bassiana* strain ATCC-74040. In another embodiment, the composition further comprises at least one fungal insecticide comprising spores of *Beauveria bassiana* strain ATCC-74040. In another particular embodiment, the composition further comprises at least one fungal insecticide comprising *Beauveria bassiana* strain ATCC-74250. In still another particular embodiment, the composition further comprises at least one fungal insecticide comprising spores of *Beauveria bassiana* strain ATCC-74250. In yet another particular embodiment, the composition further comprises at least one fungal insecticide comprising a mixture of *Beauveria bassiana* strain ATCC-74040 and *Beauveria bassiana* strain ATCC-74250. In still another embodiment, the composition further comprises at least one fungal insecticide comprising a mixture of spores of *Beauveria bassiana* strain ATCC-74040 and *Beauveria bassiana* strain ATCC-74250.

In still yet another particular embodiment, the composition described herein may comprise a combination of fungi. In one embodiment, the composition may comprise two or more fungal insecticides that are different strains of the same species. In another embodiment, the composition comprises at least two different fungal insecticides that are strains of different species. In an embodiment, the composition comprises at least one fungal insecticide from the genus *Metarhizium* spp. and at least one fungal insecticide from the genus *Beauveria* spp. In another embodiment, the composition comprises spores of *Metarhizium* spp. and *Beauveria* spp.

In a particular embodiment, the composition comprises at least one fungal insecticide, wherein at least one fungal insecticide is a strain of *Metarhizium anisopliae* and at least one fungal insecticide is a strain of *Beauveria bassiana*. In another embodiment, the composition comprises at least one fungal insecticide wherein the fungal insecticide comprises spores of *Metarhizium anisopliae* and *Beauveria bassiana*.

In a more particular embodiment, the composition comprises at least one fungal insecticide, wherein at least one fungal insecticide is a strain of *Metarhizium anisopliae* F52 and at least one fungal insecticide is a strain of the strain *Beauveria bassiana* ATCC-74040. In yet another embodiment, the composition comprises at least one fungal insecticide wherein the fungal insecticide comprises spores of the strain *Metarhizium anisopliae* F52 and the strain *Beauveria bassiana* ATCC-74040.

In still another particular embodiment, the composition comprises at least one fungal insecticide, wherein at least one fungal insecticide is a strain of *Metarhizium anisopliae* F52 and at least one fungal insecticide is a strain of the strain *Beauveria bassiana* ATCC-74250. In yet another embodiment, the composition comprises at least one fungal insecticide wherein the fungal insecticide comprises spores of the strain *Metarhizium anisopliae* F52 and the strain *Beauveria bassiana* ATCC-74250.

In still yet another particular embodiment, the composition comprises at least one fungal insecticide, wherein at least one fungal insecticide is a strain of *Metarhizium anisopliae* F52, at least one fungal insecticide is a strain of the strain *Beauveria bassiana* ATCC-74040, and at least one fungal insecticide is a strain of the strain *Beauveria bassiana* ATCC-74250. In yet another embodiment, the composition comprises at least one fungal insecticide wherein the fungal insecticide comprises spores of the strain *Metarhizium anisopliae* F52, the strain *Beauveria bassiana* ATCC-74040, and the strain *Beauveria bassiana* ATCC-74250.

In another embodiment, the composition comprises at least one fungal insecticide, wherein at least one fungal insecticide is a strain of *Paecilomyces fumosoroseus*. In yet another embodiment, the composition comprises at least one fungal insecticide, wherein at least one fungal insecticide is a strain of *Paecilomyces fumosoroseus* FE991 (in NOFLY® from FuturEco BioScience S.L., Barcelona, Spain). In still yet another embodiment, the composition comprises at least one fungal insecticide, wherein at least one fungal insecticide wherein the at least one fungal insecticide is a strain of *Paecilomyces fumosoroseus* FE991 at least one fungal insecticide is a strain of *Metarhizium anisopliae* F52, at least one fungal insecticide is a strain of the strain *Beauveria bassiana* ATCC-74040, and at least one fungal insecticide is a strain of the strain *Beauveria bassiana* ATCC-74250, and combinations thereof.

In another embodiment, the compositions disclosed herein comprise a nematicide. In a more particular embodiment, the nematicide is a microbial nematicide, more preferably a nematophagous fungus and/or nematophagous bacteria. In a particular embodiment, the microbial nematicide is a nematophagous fungus selected from the group consisting of *Arthrobotrys* spp., *Dactylaria* spp., *Harposporium* spp., *Hirsutella* spp., *Monacrosporium* spp., *Nematoctonus* spp., *Meristacrum* spp., *Myrothecium* spp., *Paecilomyces* spp., *Pasteuria* spp., *Pochonia* spp., *Trichoderma* spp.,

*Verticillium* spp., and combinations thereof. In still a more particular embodiment, the nematophagous fungus is selected from the group consisting of *Arthrobotrys dactyloides, Arthrobotrys oligospora, Arthrobotrys superb, Arthrobotrys dactyloides, Dactylaria candida, Harposporium anguillulae, Hirsutella rhossiliensis, Hirsutella minnesotensis, Monacrosporium cionopagum, Nematoctonus geogenius, Nematoctonus leiosporus, Meristacrum asterospermum, Myrothecium verrucaria, Paecilomyces lilacinus, Paecilomyces fumosoroseus, Pasteuria penetrans, Pasteuria usgae, Pochonia chlamydopora, Trichoderma harzianum, Trichoderma virens, Verticillium chlamydosporum*, and combinations thereof.

In a more particular embodiment, the microbial nematicide is a nematophagous bacteria selected from the group consisting of *Actinomycetes* spp., *Agrobacterium* spp., *Arthrobacter* spp., *Alcaligenes* spp., *Aureobacterium* spp., *Azobacter* spp., *Beijerinckia* spp., *Burkholderia* spp., *Chromobacterium* spp., *Clavibacter* spp., *Clostridium* spp., *Comomonas* spp., *Corynebacterium* spp., *Curtobacterium* spp., *Desulforibtio* spp., *Enterobacter* spp., *Flavobacterium* spp., *Gluconobacter* spp., *Hydrogenophage* spp., *Klebsiella* spp., *Methylobacterium* spp., *Phyllobacterium* spp., *Phingobacterium* spp., *Photorhabdus* spp., *Serratia* spp. *Stenotrotrophomonas* spp., *Xenorhadbus* spp. *Variovorax* spp., *Streptomyces* spp., *Pseudomonas* spp., *Paenibacillus* spp., and combinations thereof.

In still a more particular embodiment, the microbial nematicide is a nematophagous bacteria selected from the group consisting of *Chromobacterium subtsugae, Chromobacterium violaceum, Streptomyces lydicus, Streptomyces violaceusniger*, and combinations thereof. In a particular embodiment, the strain of *Chromobacterium subtsugae* is a strain of *Chromobacterium subtsugae* sp. nov., more particularly, the strain of *Chromobacterium subtsugae* sp. nov. has the deposit accession number NRRL B-30655. In still another particular embodiment, the strain of *Streptomyces* is a strain of *Streptomyces lydicus* WYEC 108, a strain of *Streptomyces violaceusniger* YCED 9, *Streptomyces* WYE53 or a combination thereof.

Nutrient(s):

In still another embodiment, the compositions described herein may further comprise one or more beneficial nutrients. Non-limiting examples of nutrients for use in the compositions described herein include vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic acid, taurine, etc.), and combinations thereof. In a particular embodiment, the compositions may comprise phosphorous, boron, chlorine, copper, iron, manganese, molybdenum, zinc or combinations thereof.

In another embodiment, the compositions described herein may further comprise phosphorus. In one embodiment, the phosphorus may be derived from a source. In another embodiment, suitable sources of phosphorus include phosphorus sources capable of solubilization by one or more microorganisms (e.g., *Penicillium bilaiae*, etc.).

In one embodiment, the phosphorus may be derived from a rock phosphate source. In another embodiment the phosphorus may be derived from fertilizers comprising one or more phosphorus sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present disclosure it is possible to reduce the amount of these fertilizers applied to the soil while still maintaining the same amount of phosphorus uptake from the soil.

In still another embodiment, the phosphorus may be derived from an organic phosphorus source. In a further particular embodiment, the source of phosphorus may include an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still another embodiment, the phosphorus may be derived from a combination of phosphorus sources including, but not limited to, rock phosphate, fertilizers comprising one or more phosphorus sources (e.g., monoammonium phosphate, diammonium phosphate, monocalcium phosphate, super phosphate, triple super phosphate, ammonium polyphosphate, etc.) one or more organic phosphorus sources, and combinations thereof.

Biostimulant(s):

In one embodiment, the compositions described herein may further comprise one or more beneficial biostimulants. Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., *ascophyllum nodosum*), humic acids (e.g., potassium humate), fulvic acids, myo-inositol, glycine, and combinations thereof. In another embodiment, the compositions comprise seaweed extracts, humic acids, fulvic acids, myo-inositol, glycine, and combinations thereof.

Polymer(s):

In one embodiment, the compositions described herein may further comprise one or more polymers. Non-limiting uses of polymers in the agricultural industry include agrochemical delivery, heavy metal removal, water retention and/or water delivery, and combinations thereof. Pouci, et al., Am. J. Agri. & Biol. Sci., 3(1):299-314 (2008). In one embodiment, the one or more polymers is a natural polymer (e.g., agar, starch, alginate, pectin, cellulose, etc.), a synthetic polymer, a biodegradable polymer (e.g., polycaprolactone, polylactide, poly (vinyl alcohol), etc.), or a combination thereof.

For a non-limiting list of polymers useful for the compositions described herein, see Pouci, et al., Am. J. Agri. & Biol. Sci., 3(1):299-314 (2008). In one embodiment, the compositions described herein comprise cellulose, cellulose derivatives, methylcellulose, methylcellulose derivatives, starch, agar, alginate, pectin, polyvinylpyrrolidone, and combinations thereof.

Wetting Agent(s):

In one embodiment, the compositions described herein may further comprise one or more wetting agents. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an embodiment, the wetting agent is a surfactant. In an embodiment, the wetting agent is one or more nonionic surfactants, one or more anionic surfactants, or a combination thereof. In yet another embodiment, the wetting agent is one or more nonionic surfactants.

Surfactants suitable for the compositions described herein are provided in the "Surfactants" section.

Surfactant(s):

Surfactants suitable for the compositions described herein may be non-ionic surfactants (e.g., semi-polar and/or anionic and/or cationic and/or zwitterionic). The surfactants can wet and emulsify soil(s) and/or dirt(s). It is envisioned that the surfactants used in described composition have low toxicity for any microorganisms contained within the formulation. It is further envisioned that the surfactants used in the described composition have a low phytotoxicity (i.e., the degree of toxicity a substance or combination of substances has on a plant). A single surfactant or a blend of several surfactants can be used.

Anionic Surfactants

Anionic surfactants or mixtures of anionic and nonionic surfactants may also be used in the compositions. Anionic surfactants are surfactants having a hydrophilic moiety in an anionic or negatively charged state in aqueous solution. The compositions described herein may comprise one or more anionic surfactants. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof. Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Nonionic Surfactants

Nonionic surfactants are surfactants having no electrical charge when dissolved or dispersed in an aqueous medium. In at least one embodiment of the composition described herein, one or more nonionic surfactants are used as they provide the desired wetting and emulsification actions and do not significantly inhibit spore stability and activity. The nonionic surfactant(s) may be either water soluble nonionic surfactants, water insoluble nonionic surfactants, or a combination of water soluble nonionic surfactants and water insoluble nonionic surfactants.

Water Insoluble Nonionic Surfactants

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, or combinations thereof. Also included are EO/PO block copolymers (EO is ethylene oxide, PO is propylene oxide), EO polymers and copolymers, polyamines, and polyvinylpynolidones.

Water Soluble Nonionic Surfactants

Non-limiting examples of water soluble nonionic surfactants include sorbitan fatty acid alcohol ethoxylates and sorbitan fatty acid ester ethoxylates.

Combination of Nonionic Surfactants

In one embodiment, the compositions described herein comprise at least one or more nonionic surfactants. In one embodiment, the compositions comprise at least one water insoluble nonionic surfactant and at least one water soluble nonionic surfactant. In still another embodiment, the compositions comprise a combination of nonionic surfactants having hydrocarbon chains of substantially the same length.

Other Surfactants

In another embodiment, the compositions described herein may also comprise organosilicone surfactants, silicone-based antifoams used as surfactants in silicone-based and mineral-oil based antifoams. In yet another embodiment, the compositions described herein may also comprise alkali metal salts of fatty acids (e.g., water soluble alkali metal salts of fatty acids and/or water insoluble alkali metal salts of fatty acids).

Anti-Freezing Agent(s):

In one embodiment, the compositions described herein may further comprise one or more anti-freezing agents. Non-limiting examples of anti-freezing agents include ethylene glycol, propylene glycol, urea, glycerin, and combinations thereof.

Methods

In another aspect, methods of using one or more microbially stabilizing compounds to increase the survivability of one or more microorganisms are disclosed. In a particular embodiment, the method includes adding one or more microbially stabilizing compounds as described herein to a mixture comprising one or more antimicrobial compounds to inhibit the antimicrobial activity of the antimicrobial compound. In yet another embodiment, the method comprises the step of adding one or more microorganisms to the mixture. In still yet another embodiment, the one or more microorganisms added to the mixture are one or more beneficial microorganisms. In a particular embodiment, the mixture is a seed treatment composition.

Still further, the method of using one or more microbially stabilizing compounds to increase the survivability of one or more microorganisms further comprises the step of adding one or more agriculturally beneficial ingredients as described herein. In one embodiment, the step of adding one or more agriculturally beneficial ingredients may occur before, after, or simultaneously with the step of adding one or more microbially stabilizing compounds to a mixture. In still another embodiment, the step of adding one or more agriculturally beneficial ingredients may occur before, after, or simultaneously with the step of adding one or more microbes to the mixture.

Seed Coatings

In another aspect, seeds are coated with one or more compositions described herein.

In another embodiment, the method further comprises a method for coating a seed comprising adding one or more microbially stabilizing compounds as described herein to a mixture comprising one or more antimicrobial compounds to inhibit the antimicrobial activity of the antimicrobial compound, adding one or more microorganisms to the mixture, and applying the mixture to a seed. In still yet another embodiment, the one or more microorganisms added to the mixture are one or more beneficial microorganisms. In a particular embodiment, the mixture is a seed treatment composition.

The applying step can be performed by any method known in the art. Non-limiting examples of applying to a seed include, but are not limited to, spraying a seed, drenching a seed, dripping on a seed, dusting a seed, submerging a seed, and/or coating a seed. In a more particular embodiment, the applying step is a seed coating step. In a further embodiment, the applying step is repeated (e.g., more than once, as in the contacting step is repeated twice, three times, four times, five times, six times, seven times, eight times, nine times, ten times, etc.).

Still further, the method of for coating a seed further comprises the step of adding one or more agriculturally beneficial ingredients as described herein. In one embodiment, the step of adding one or more agriculturally beneficial ingredients may occur before, after, or simultaneously with the step of adding a mixture one or more antimicrobial compounds to inhibit the antimicrobial activity of the antimicrobial compound. In still another embodiment, the step of adding one or more agriculturally beneficial ingredients may occur before, after, or simultaneously with the step of adding one or more microorganisms to the mixture. In still yet another embodiment, the step of adding one or more agriculturally beneficial ingredients may occur before, after, or simultaneously with the step of applying the mixture to a seed In one embodiment, seeds may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition(s) described herein, adding seeds, then rotating the container to cause the seeds to contact the wall and the composition(s), a process known in the art as "container coating". Seeds can be coated by combinations of coating methods. Soaking typically entails using liquid forms of the compositions described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

The embodiments of the disclosure are further defined by the following numbered paragraphs:

1. A method for increasing the survivability of one or more beneficial microorganisms comprising adding to a seed treatment composition one or more microbially stabilizing compounds which inhibits the antimicrobial activity of one or more antimicrobial compounds.

2. The method of paragraph 1, wherein the method further comprises the step of adding one or more beneficial microorganisms to the seed treatment composition.

3. The method of paragraphs 1 or 2, wherein the one or more beneficial microorganisms is a nitrogen fixing microorganism, a phosphate solubilizing microorganism, or a combination thereof.

4. The method of paragraph 1 or 2, wherein the one or more beneficial microorganisms is a nitrogen fixing microorganism.

5. The method of paragraph 1 or 2, wherein the one or more beneficial microorganisms is a phosphate solubilizing microorganism.

6. The method of paragraphs 3-4, wherein the nitrogen fixing microorganism is a species of *Rhizobia* selected from the group consisting of *Rhizobium* spp., *Bradyrhizobium* spp., *Azorhizobium* spp., *Sinorhizobium* spp., *Mesorhizobium* spp., *Azospirillum* spp., and combinations thereof.

7. The method of paragraph 6, wherein the nitrogen fixing microorganism is a species of bacteria selected from the group consisting of *Rhizobium cellulosilyticum, Rhizobium daejeonense, Rhizobium etli, Rhizobium galegae, Rhizobium gallicum, Rhizobium giardinii, Rhizobium hainanense, Rhizobium huautlense, Rhizobium indigoferae, Rhizobium leguminosarum, Rhizobium loessense, Rhizobium lupini, Rhizobium lusitanum, Rhizobium meliloti, Rhizobium mongolense, Rhizobium miluonense, Rhizobium sullae, Rhizobium tropici, Rhizobium undicola, Rhizobium yanglingense, Bradyrhizobium bete, Bradyrhizobium canariense, Bradyrhizobium elkanii, Bradyrhizobium iriomotense, Bradyrhizobium japonicum, Bradyrhizobium jicamae, Bradyrhizobium liaoningense, Bradyrhizobium pachyrhizi, Bradyrhizobium yuanmingense, Azorhizobium caulinodans, Azorhizobium doebereinerae, Sinorhizobium abri, Sinorhizobium adhaerens, Sinorhizobium americanum, Sinorhizobium aboris Sinorhizobium fredii, Sinorhizobium indiaense, Sinorhizobium kostiense, Sinorhizobium kummerowiae, Sinorhizobium medicae, Sinorhizobium meliloti, Sinorhizobium mexicanus, Sinorhizobium morelense, Sinorhizobium saheli, Sinorhizobium terangae, Sinorhizobium xinjiangense, Mesorhizobium albiziae, Mesorhizobium amorphae, Mesorhizobium chacoense, Mesorhizobium ciceri, Mesorhizobium huakuii, Mesorhizobium loti, Mesorhizobium mediterraneum, Mesorhizobium pluifarium, Mesorhizobium septentrionale, Mesorhizobium temperatum, Mesorhizobium tianshanense, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae*, and combinations thereof.

8. The method of paragraphs 3 or 5, wherein the phosphate solubilizing microorganism is a species selected from the group consisting of *Acinetobacter* spp., *Arthrobacter* spp, *Arthrobotrys* spp., *Aspergillus* spp., *Azospirillum* spp., *Bacillus* spp., *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., and combinations thereof.

9. The method of paragraph 8, wherein the phosphate solubilizing microorganism is a species of *Penicillium* spp. selected from the group consisting of *Penicillium bilaiae, Penicillium albidum, Penicillium aurantiogriseum, Penicillium chrysogenum, Penicillium citreonigrum, Penicillium citrinum, Penicillium digitatum, Penicillium frequentas, Penicillium fuscum, Penicillium gaestrivorus, Penicillium glabrum, Penicillium griseofulvum, Penicillium implicatum, Penicillium janthinellum, Penicillium lilacinum, Penicillium minioluteum, Penicillium montanense, Penicillium nigricans, Penicillium oxalicum, Penicillium pinetorum, Penicillium pinophilum, Penicillium purpurogenum, Penicillium radicans, Penicillium radicum, Penicillium raistrickii, Penicillium rugulosum, Penicillium simplicissimum, Penicillium solitum, Penicillium variabile, Penicillium velutinum, Penicillium viridicatum, Penicillium glaucum, Penicillium fussiporus, Penicillium expansum*, and combinations thereof.

10. The method of paragraph 1, wherein the one or more microbially stabilizing compounds is a compound selected from the group consisting of yeast extract, calcium caseinate, milk, urea, hematinic agents, beef extract, ammonia, amino acids, ammonium salts, ferric salts, ferrous salts, gluconolactone, glutathione, lecithin, polysorbates, albumin, peptones, and combinations thereof.

11. The method of paragraph 1, wherein the one or more antimicrobial compounds is a bacteriostat, a bactericide, or a combination thereof.

12. The method of paragraph 11, wherein the bactericide is a disinfectant, an antiseptic, or an antibiotic.

13. The method of paragraph 12, wherein the disinfectant is selected from the group consisting of active chlorine, active oxygen, iodine, alcohols, phenolic substances, cationic surfactants, strong oxidizers, heavy metals and their salts, acids, and alkalis.

14. The method of paragraph 12, wherein the antiseptic is selected from the group consisting of chlorine preparations, iodine preparations, peroxides, alcohols, organic acids, phenolic compounds, cation-active compounds.

15. The method of paragraph 12, wherein the antibiotic is selected from the group consisting of penicillin, cephalosporins, aminoglycosidic antibiotics, fluoroquinolones, nitrofurans, vancomycin, monobactams, co-trimoxazole, and metronidazole.

16. The method of paragraph 11, wherein the bacteriostat is sodium azide or thimerosol.

17. The method of paragraph 1, wherein the one or more antimicrobial compounds is selected from the group consisting of formaldhyde, benzyl-hemiformal (phenylmethoxymethanol), 2-bromo-2-nitro-1,3-propanadiol, 1-(3-chloroallyl)-3,5,7-triaza-1-azoniaadamantane chloride, dibromonitrilopropionamide, 1,2-benzisothiazolin-3-one, 5-chloro-2-methyl-4-isothiazolin-3-one, 2-methyl-4-isothiazolin-3-one, diazolidinyl urea, tris(hydroxymethyl)nitromethane, sodium o-phenylphenate, copper arsenates, cuprous oxide, compounds of arsenic, copper, mercury, quaternary ammonium compounds, sodium azide, thimerosol, or combinations thereof.

18. The method of paragraph 1, wherein the method further comprises the step of adding one or more agriculturally beneficial ingredients.

19. The method of paragraph 18, wherein adding one or more agriculturally beneficial ingredients occurs after the step of adding to a seed treatment composition one or more microbially stabilizing compounds which inhibits the antimicrobial activity of one or more antimicrobial compounds.

20. The method of paragraph 2, wherein adding one or more agriculturally beneficial ingredients occurs after the step of adding one or more beneficial microorganisms to the seed treatment composition.

21. The method of paragraph 18, wherein adding one or more agriculturally beneficial ingredients occurs simultaneously with the step of adding to a seed treatment composition one or more microbially stabilizing compounds which inhibits the antimicrobial activity of one or more antimicrobial compounds.

22. The method of paragraph 20, wherein adding one or more agriculturally beneficial ingredients occurs simultaneously with the step of adding one or more beneficial microorganisms to the seed treatment composition.

23. The method of paragraphs 18-22, wherein the one or more agriculturally beneficial ingredients are one or more plant signal molecules selected from the group consisting of lipo-chitooligosaccharides (LCOs), chitooligosaccharides (COs), chitinous compounds, flavonoids, jasmonic acid, methyl jasmonate, linoleic acid, linolenic acid, karrikins, and combinations thereof.

24. The method of paragraph 23, wherein the one or more agriculturally beneficial ingredients comprises one or more COs.

25. The method of paragraph 23, wherein the one or more agriculturally beneficial ingredients comprises one or more LCOs.

26. The method of paragraph 23, wherein the one or more agriculturally beneficial ingredients comprises one or more flavonoids.

27. A method for coating a seed, comprising applying a seed treatment composition to a seed, wherein the seed treatment composition comprises one or more beneficial microorganisms and one or more microbially stabilizing compounds which inhibits the antimicrobial activity of one or more antimicrobial compounds.

28. The method of paragraph 27, wherein the one or more beneficial microorganisms is a nitrogen fixing microorganism, a phosphate solubilizing microorganism, or a combination thereof.

29. The method of paragraph 27, wherein the one or more beneficial microorganisms is a nitrogen fixing microorganism.

30. The method of paragraph 27, wherein the one or more beneficial microorganisms is a phosphate solubilizing microorganism.

31. The method of paragraph 29, wherein the nitrogen fixing microorganism is a species of *Rhizobia* selected from the group consisting of *Rhizobium* spp., *Bradyrhizobium* spp., *Azorhizobium* spp., *Sinorhizobium* spp., *Mesorhizobium* spp., *Azospirillum* spp., and combinations thereof.

32. The method of paragraph 31, wherein the nitrogen fixing microorganism is a species of bacteria selected from the group consisting of *Rhizobium cellulosilyticum, Rhizobium daejeonense, Rhizobium etli, Rhizobium galegae, Rhizobium gallicum, Rhizobium giardinii, Rhizobium hainanense, Rhizobium huautlense, Rhizobium indigoferae, Rhizobium leguminosarum, Rhizobium loessense, Rhizobium lupini, Rhizobium lusitanum, Rhizobium meliloti, Rhizobium mongolense, Rhizobium miluonense, Rhizobium sullae, Rhizobium tropici, Rhizobium undicola, Rhizobium yanglingense, Bradyrhizobium bete, Bradyrhizobium canariense, Bradyrhizobium elkanii, Bradyrhizobium iriomotense, Bradyrhizobium japonicum, Bradyrhizobium jicamae, Bradyrhizobium liaoningense, Bradyrhizobium pachyrhizi, Bradyrhizobium yuanmingense, Azorhizobium caulinodans, Azorhizobium doebereinerae, Sinorhizobium abri,*

*Sinorhizobium adhaerens, Sinorhizobium americanum, Sinorhizobium aboris Sinorhizobium fredii, Sinorhizobium indiaense, Sinorhizobium kostiense, Sinorhizobium kummerowiae, Sinorhizobium medicae, Sinorhizobium meliloti, Sinorhizobium mexicanus, Sinorhizobium morelense, Sinorhizobium saheli, Sinorhizobium terangae, Sinorhizobium xinjiangense, Mesorhizobium albiziae, Mesorhizobium amorphae, Mesorhizobium chacoense, Mesorhizobium ciceri, Mesorhizobium huakuii, Mesorhizobium loti, Mesorhizobium mediterraneum, Mesorhizobium pluifarium, Mesorhizobium septentrionale, Mesorhizobium temperatum, Mesorhizobium tianshanense, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae*, and combinations thereof.

33. The method of paragraph 30, wherein the phosphate solubilizing microorganism is a species selected from the group consisting of *Acinetobacter* spp., *Arthrobacter* spp, *Arthrobotrys* spp., *Aspergillus* spp., *Azospirillum* spp., *Bacillus* spp., *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., and combinations thereof.

34. The method of paragraph 33, wherein the phosphate solubilizing microorganism is a species of *Penicillium* spp. selected from the group consisting of *Penicillium bilaiae, Penicillium albidum, Penicillium aurantiogriseum, Penicillium chrysogenum, Penicillium citreonigrum, Penicillium citrinum, Penicillium digitatum, Penicillium frequentas, Penicillium fuscum, Penicillium gaestrivorus, Penicillium glabrum, Penicillium griseofulvum, Penicillium implicatum, Penicillium janthinellum, Penicillium lilacinum, Penicillium minioluteum, Penicillium montanense, Penicillium nigricans, Penicillium oxalicum, Penicillium pinetorum, Penicillium pinophilum, Penicillium purpurogenum, Penicillium radicans, Penicillium radicum, Penicillium raistrickii, Penicillium rugulosum, Penicillium simplicissimum, Penicillium solitum, Penicillium variabile, Penicillium velutinum, Penicillium viridicatum, Penicillium glaucum, Penicillium fussiporus, Penicillium expansum*, and combinations thereof.

35. The method of paragraph 27, wherein the one or more microbially stabilizing compounds is a compound selected from the group consisting of yeast extract, calcium caseinate, milk, urea, hematinic agents, beef extract, ammonia, amino acids, ammonium salts, ferric salts, ferrous salts, gluconolactone, glutathione, lecithin, polysorbates, albumin, peptones, and combinations thereof.

36. The method of paragraph 27, wherein the one or more antimicrobial compounds is a bacteriostat, a bactericide, or a combination thereof.

37. The method of paragraph 36, wherein the bactericide is a disinfectant, an antiseptic, or an antibiotic.

38. The method of paragraph 37, wherein the disinfectant is selected from the group consisting of active chlorine, active oxygen, iodine, alcohols, phenolic substances, cationic surfactants, strong oxidizers, heavy metals and their salts, acids, and alkalis.

39. The method of paragraph 37, wherein the antiseptic is selected from the group consisting of chlorine preparations, iodine preparations, peroxides, alcohols, organic acids, phenolic compounds, cation-active compounds.

40. The method of paragraph 37, wherein the antibiotic is selected from the group consisting of penicillin, cephalosporins, aminoglycosidic antibiotics, fluoroquinolones, nitrofurans, vancomycin, monobactams, co-trimoxazole, and metronidazole.

41. The method of paragraph 36, wherein the bacteriostat is sodium azide or thimerosol.

42. The method of paragraph 27, wherein the one or more antimicrobial compounds is selected from the group consisting of formaldhyde, benzyl-hemiformal (phenyl-methoxymethanol), 2-bromo-2-nitro-1,3-propanadiol, 1-(3-chloroallyl)-3,5,7-triaza-1-azoniaadamantane chloride, dibromonitrilopropionamide, 1,2-benzisothiazolin-3-one, 5-chloro-2-methyl-4-isothiazolin-3-one, 2-methyl-4-isothiazolin-3-one, diazolidinyl urea, tris(hydroxymethyl)nitromethane, sodium o-phenylphenate, copper arsenates, cuprous oxide, compounds of arsenic, copper, mercury, quaternary ammonium compounds, sodium azide, thimerosol, or combinations thereof.

43. The method of paragraph 27, wherein the method further comprises the step of adding one or more agriculturally beneficial ingredients.

44. The method of paragraph 43, wherein adding one or more agriculturally beneficial ingredients occurs after the step of applying the seed treatment composition to a seed, wherein the seed treatment composition comprises one or more beneficial microorganisms and one or more microbially stabilizing compounds which inhibits the antimicrobial activity of one or more antimicrobial compounds.

45. The method of paragraph 43, wherein adding one or more agriculturally beneficial ingredients occurs simultaneously with the step of applying the seed treatment composition to a seed, wherein the seed treatment composition comprises one or more beneficial microorganisms and one or more microbially stabilizing compounds which inhibits the antimicrobial activity of one or more antimicrobial compounds.

46. The method of paragraphs 43-45, wherein the one or more agriculturally beneficial ingredients are one or more plant signal molecules selected from the group consisting of LCOs, COs, chitinous compounds, flavonoids, jasmonic acid, methyl jasmonate, linoleic acid, linolenic acid, karrikins, and combinations thereof.

47. The method of paragraph 46, wherein the one or more agriculturally beneficial ingredients comprises one or more COs.

48. The method of paragraph 46, wherein the one or more agriculturally beneficial ingredients comprises one or more LCOs.

49. The method of paragraph 46, wherein the one or more agriculturally beneficial ingredients comprises one or more flavonoids.

50. A composition comprising:
   1) at least one compound comprising one or more microbially stabilizing compounds; and
   2) at least one second ingredient selected from groups (A) to (F)
      (A) a fungicide;
      (B) an insecticide;
      (C) a nematicide;
      (D) an acaricide;
      (E) an herbicide; and
      (F) a fertilizer.

51. The composition of paragraph 50, wherein the one or more microbially stabilizing compounds is a compound selected from the group consisting of yeast extract, calcium caseinate, milk, urea, hematinic agents, beef extract, ammonia, amino acids, ammonium salts, ferric salts, ferrous salts, gluconolactone, glutathione, lecithin, polysorbates, albumin, peptones, and combinations thereof.

52. The composition of paragraph 50, wherein the at least one second ingredient selected from groups (A) to (F) comprises one or more antimicrobial compounds.

53. The composition of paragraph 52, wherein the one or more antimicrobial compounds is a bacteriostat, a bactericide, or a combination thereof.

54. The composition of paragraph 53, wherein the bactericide is a disinfectant, an antiseptic, or an antibiotic.

55. The composition of paragraph 54, wherein the disinfectant is selected from the group consisting of active chlorine, active oxygen, iodine, alcohols, phenolic substances, cationic surfactants, strong oxidizers, heavy metals and their salts, acids, and alkalis.

56. The composition of paragraph 54, wherein the antiseptic is selected from the group consisting of chlorine preparations, iodine preparations, peroxides, alcohols, organic acids, phenolic compounds, cation-active compounds.

57. The composition of paragraph 54, wherein the antibiotic is selected from the group consisting of penicillin, cephalosporins, aminoglycosidic antibiotics, fluoroquinolones, nitrofurans, vancomycin, monobactams, co-trimoxazole, and metronidazole.

58. The composition of paragraph 53, wherein the bacteriostat is sodium azide or thimerosol.

59. The composition of paragraph 52, wherein the one or more antimicrobial compounds is selected from the group consisting of formaldehyde, benzyl-hemiformal (phenyl-methoxymethanol), 2-bromo-2-nitro-1,3-propanadiol, 1-(3-chloroallyl)-3,5,7-triaza-1-azoniaadamantane chloride, dibromonitrilopropionamide, 1,2-benzisothiazolin-3-one, 5-chloro-2-methyl-4-isothiazolin-3-one, 2-methyl-4-isothiazolin-3-one, diazolidinyl urea, tris(hydroxymethyl)nitromethane, sodium o-phenylphenate, copper arsenates, cuprous oxide, compounds of arsenic, copper, mercury, quaternary ammonium compounds, sodium azide, thimerosol, or combinations thereof.

60. The composition of paragraph 50, wherein the composition further comprises one or more agriculturally beneficial ingredients.

61. The composition of paragraph 60, wherein the one or more agriculturally beneficial ingredients are one or more plant signal molecules selected from the group consisting of LCOs, COs, chitinous compounds, flavonoids, jasmonic acid, methyl jasmonate, linoleic acid, linolenic acid, karrikins, and combinations thereof.

62. The composition of paragraph 61, wherein the one or more agriculturally beneficial ingredients comprises one or more COs.

63. The composition of paragraph 61, wherein the one or more agriculturally beneficial ingredients comprises one or more LCOs.

64. The composition of paragraph 61, wherein the one or more agriculturally beneficial ingredients comprises one or more flavonoids.

65. The composition of paragraph 61, wherein the composition further comprises one or more beneficial microorganisms.

66. The composition of paragraph 65, wherein the one or more beneficial microorganisms is a nitrogen fixing microorganism, a phosphate solubilizing microorganism, or a combination thereof.

67. The composition of paragraph 66, wherein the one or more beneficial microorganisms is a nitrogen fixing microorganism.

68. The composition of paragraph 66, wherein the one or more beneficial microorganisms is a phosphate solubilizing microorganism.

69. The composition of paragraphs 66-67, wherein the nitrogen fixing microorganism is a species of *Rhizobia* selected from the group consisting of *Rhizobium* spp., *Bradyrhizobium* spp., *Azorhizobium* spp., *Sinorhizobium* spp., *Mesorhizobium* spp., *Azospirillum* spp., and combinations thereof.

70. The composition of paragraph 69, wherein the nitrogen fixing microorganism is a species of bacteria selected from the group consisting of *Rhizobium cellulosilyticum, Rhizobium daejeonense, Rhizobium etli, Rhizobium galegae, Rhizobium gallicum, Rhizobium giardinii, Rhizobium hainanense, Rhizobium huautlense, Rhizobium indigoferae, Rhizobium leguminosarum, Rhizobium loessense, Rhizobium lupini, Rhizobium lusitanum, Rhizobium meliloti, Rhizobium mongolense, Rhizobium miluonense, Rhizobium sullae, Rhizobium tropici, Rhizobium undicola, Rhizobium yanglingense, Bradyrhizobium bete, Bradyrhizobium canariense, Bradyrhizobium elkanii, Bradyrhizobium iriomotense, Bradyrhizobium japonicum, Bradyrhizobium jicamae, Bradyrhizobium liaoningense, Bradyrhizobium pachyrhizi, Bradyrhizobium yuanmingense, Azorhizobium caulinodans, Azorhizobium doebereinerae, Sinorhizobium abri, Sinorhizobium adhaerens, Sinorhizobium americanum, Sinorhizobium aboris Sinorhizobium fredii, Sinorhizobium indiaense, Sinorhizobium kostiense, Sinorhizobium kummerowiae, Sinorhizobium medicae, Sinorhizobium meliloti, Sinorhizobium mexicanus, Sinorhizobium morelense, Sinorhizobium saheli, Sinorhizobium terangae, Sinorhizobium xinjiangense, Mesorhizobium albiziae, Mesorhizobium amorphae, Mesorhizobium chacoense, Mesorhizobium ciceri, Mesorhizobium huakuii, Mesorhizobium loti, Mesorhizobium mediterraneum, Mesorhizobium pluifarium, Mesorhizobium septentrionale, Mesorhizobium temperatum, Mesorhizobium tianshanense, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae*, and combinations thereof.

71. The composition of paragraphs 66 or 68, wherein the phosphate solubilizing microorganism is a species selected from the group consisting of *Acinetobacter* spp., *Arthrobacter* spp, *Arthrobotrys* spp., *Aspergillus* spp., *Azospirillum* spp., *Bacillus* spp., *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., and combinations thereof.

72. The composition of paragraph 71, wherein the phosphate solubilizing microorganism is a species of *Penicillium* spp. selected from the group consisting of *Penicillium* bilaiae, Penicillium albidum, Penicillium aurantiogriseum, Penicillium chrysogenum, Penicillium citreonigrum, Penicillium citrinum, Penicillium digitatum, Penicillium frequentas, Penicillium fuscum, Penicillium gaestrivorus, Penicillium glabrum, Penicillium griseofulvum, Penicillium implicatum, Penicillium janthinellum, Penicillium lilacinum, Penicillium miniluteum, Penicillium montanense, Penicillium nigricans, Penicillium oxalicum, Penicillium pinetorum, Penicillium pinophilum, Penicillium purpurogenum, Penicillium radicans, Penicillium radicum, Penicillium raistrickii, Penicillium rugulosum, Penicillium simplicissimum, Penicillium solitum, Penicillium variabile, Penicillium velutinum, Penicillium viridicatum, Penicillium glaucum, Penicillium fussiporus, Penicillium expansum, and combinations thereof.

EXAMPLES

The following examples are provided for illustrative purposes and are not intended to limit the scope of the embodiments as claimed herein. Any variations in the exemplified examples which occur to the skilled artisan are intended to fall within the scope of the present disclosure.

Materials:

| YEM-agar (g · l$^{-1}$) |
| --- |
| Mannitol (10.0) |
| K$_2$HPO$_4$ (0.5) |
| Yeast extract (0.5) |
| MgSO$_4$•7H$_2$O, (0.2) |
| NaCl (0.007) |
| YEM-PCNB - Congo Red - Vancomycin Agar (g · l$^{-1}$) |
| Mannitol (10.0) |
| K$_2$HPO$_4$ (0.5) |
| Yeast extract (0.5) |
| MgSO$_4$•7H$_2$O, (0.2) |
| NaCl (0.007) |
| Congo Red (0.04) |
| PCNB (0.2) |
| Vancomycin (0.001) |
| Saline Solution* |
| NaCL 8.5 g |
| Distilled H$_2$O |
| Microbes |
| *Bradyrhizobium elkani* SEMIA 587 |
| *Bradyrhizobium elkani* SEMIA 5019 |
| *Bradyrhizobium japonicum* SEMIA 5079 |
| *Bradyrhizobium japonicum* SEMIA 5080 |

*Sterilized via autoclaving

Example 1

The activity of two microbially stabilizing compounds, yeast extract and albumin, were tested for reducing the effects of the preservative benzyl hemi-formal (at a concentration reflecting that provided by the current recommendation for a commercial insecticide that includes that preservative).

Using conventional aseptic techniques, 10 ml of a commercial liquid inoculant containing *B. elkani* SEMIA 587 and *B. elkani* SEMIA 5019 (Nitragin Optimize II, commercially available from Novozymes) was transferred to a series of sterile test tubes, to which 0.7 ml of a 2% solution containing benzyl hemi-formal was added and, in the corresponding tubes, 0.3 g of Yeast extract (commercially available from Merck) or 0.3 g Albumin (commercially available from SIGMA) were incorporated. A control of bacterial survival consisting of the inoculants without a microbial stabilizing compound was tested for comparison. The treatments are provided in Table 1.

TABLE 1

| | | Treatments | | |
| --- | --- | --- | --- | --- |
| Treatment | Inoculant | Benzyl hemi-formal (final concentration) | Yeast extract (final concentration) | Albumin (final concentration |
| 1 | 10 ml | 0.14% w/v | | |
| 2 | 10 ml | 0.14% w/v | 0.03% w/v | |
| 3 | 10 ml | 0.14% w/v | | 0.03% w/v |
| 4 | 10 ml | | | |

The tubes were mixed using a vortex agitator, transferred to a 30° C. orbital shaker. After 20 minutes incubation (Time 0), 0.1 ml samples were taken, and conventionally diluted 1/10 in a series of tubes containing 0.9 ml of sterile saline solution (0.85% NaCl in distilled water). 0.1 ml of dilutions $10^{-5}$, $10^{-6}$ and, $10^{-7}$ were plated in triplicate on Yeast Extract Mannitol Agar (YEM). The plates were incubated at 30° C. Colonies were counted after seven days incubation. The number of colony forming units per ml (CFU ml$^{-1}$) was calculated taking into account the plated dilutions and the plated volume. Samples were obtained and processed as above at two hours intervals. Results are indicated in Table 2.

TABLE 2

Effect of Yeast Extract and Albumin on Inoculant Survivability in the Presence of Benzyl Hemi-Formal Over Time

| Treatment | 0 hs | 2 hs | 4 hs |
| --- | --- | --- | --- |
| 1 | 3.00E+09 | 1.00E+08 | BDL* |
| 2 | 4.00E+09 | 3.50E+09 | 7.00E+08 |
| 3 | 3.40E+09 | 5.50E+08 | 5.50E+07 |
| 4 | 3.40E+09 | 3.50E+09 | 3.00E+09 |

*BDL: Below Detection Limits (10$^6$ CFU/ml)

As shown in Table 2, yeast extract and albumin reduce the deleterious effects induced by the presence of benzyl hemi-formal at the concentration tested.

Example 2

The general protocol described in Example 1 was modified to process larger samples. A commercial insecticide containing benzyl hemi-formal was tested at concentrations that would emulate the recommended doses both for the inoculants and the insecticide.

Sterile 250 ml erlenmeyers containing sterile magnetic stirrers were used instead of test tubes. The volumes of each solution are provided in Table 3. The commercial insecticide was transferred to a series of erlenmeyers and the stated amounts of microbial stabilizing compounds (yeast extract and soy meal peptone from Merck and tryptophan from Ajinomoto) were premixed at 250 rpm for 6 hours.

TABLE 3

| Treatment | Inoculant (30 ml) | Insecticide (30 ml) | Yeast extract (3 g) | Peptone from soymeal (3 g) | Tryptophan (1 g) |
|---|---|---|---|---|---|
| 1 | X | X | | | |
| 2 | X | X | X | | |
| 3 | X | X | | X | |
| 4 | X | X | | | X |
| 5 | X | | | | |

To each of the corresponding erlenemeyer flasks, 30 ml of the inoculants (as described in example 1) was added, mixed, and samples were obtained immediately and at 2 hr intervals. Samples were processed as described in Example 1. Results are provided in Table 4.

TABLE 4

Effect of Yeast Extract and Peptone from soy meal on Inoculant Survivability in the Presence of Insecticide Containing Benzyl Hemi-Formal Over Time

| | cfu/ml | | | |
|---|---|---|---|---|
| Treatment | 0 hs | 2 hs | 4 hs | 6 hs |
| 1 | 2.00E+09 | 1.00E+08 | BDL* | BDL* |
| 2 | 3.30E+09 | 3.50E+09 | 2.00E+09 | 1.00E+09 |
| 3 | 3.40E+09 | 2.20E+09 | 3.00E+09 | 1.10E+09 |
| 4 | 4.00E+09 | 3.50E+09 | 4.20E+09 | 3.90E+09 |
| 5 | 3.40E+09 | 4.00E+09 | 3.33E+09 | 3.30E+09 |

*BDL: Below detection limits ($10^6$ CFU/ml)

As shown in Table 4, yeast extract, peptone from soy meal, and tryptophan, reduce the deleterious effects induced by the presence of benzyl hemi-formal containing agrochemical on a microbial population.

Example 3

Yeast extract and calcium caseinate were used in a peat based preinoculation system containing *B. elkani* SEMIA 587 and *B. elkani* SEMIA 5019 (Nitragin CTS200, available from Novozymes) and tested for compatibility with benzyl hemi-formal containing agrochemicals for on seed stability. Seed treatment is done following the protocol described herein.

Yeast extract or calcium caseinate (from Merck) were premixed using magnetic stirrers for 6 hours with the benzyl hemi-formal containing agrochemical. After 6 hours, the seeds were treated. Table 5 describes the seed treatments corresponding to 1 kg seed.

TABLE 5

| Treatments | Treatment Number | | |
|---|---|---|---|
| | 1 | 2 | 3 |
| Nitragin CTS200 | 8.5 g | 8.5 g | 8.5 g |
| Benzyl hemi-formal containing insecticide | 3 ml | 3 ml | 3 ml |
| Yeast extract | | 0.3 g | |
| Calcium caseinate | | | 0.3 g |

For treatments combining liquid inoculants and other products (fungicides, insecticides, etc), the treatment was prepared according to instructions and let stand at room temperature for half an hour before inoculating seeds.

Seeds were placed inside a polyethylene bag and the treatment was added. The seeds must occupy ⅓ of the total volume of the bag (inflated and closed). The contents of the bag were mixed vigorously with rotating movements for proper distribution of the products inside.

The bag with the inoculated seeds was opened and left to sit at room temperature for 4 hours and on seed rhizobial counts were made. For this, 100 seeds were placed in a 250 ml Erlenmeyer with 100 ml of saline solution and subjected to shaking for 15 min using magnetic stirrer at approximately 300 rpm. The supernatant is named the dilution 10°. 1 ml samples were taken, and conventionally diluted 1/10 in a series of tubes containing 9 ml of sterile saline solution (0.85% NaCl in distilled water). 0.1 ml of dilutions $10^{-1}$, $10^{-2}$, $10^{-3}$ and $10^{-4}$ were plated in triplicate on Yeast Extract Mannitol Agar (YEM).

Seeds were then placed in paper bags and kept in a 30° C. chamber until the end of the test. Determinations were repeated at 24 and 48 hours after inoculation. Plates were read after seven days and checked on day ten. Plates were counted having between 30 and 300 colonies and the ratio between dilutions was checked. The $CFU.seed^{-1}$ according to formula (I) was calculated. Results are provided in Table 6.

$$CFU.seed^{-1} = N^{o} \text{ of colonies counted} \times 10 \times \text{dilution factor} \quad \text{Formula (I)}$$

TABLE 6

Effect of Yeast Extract and Calcium Caseinate on On-Seed Microbial Survivability when using Benzyl Hemi-Formal containing agrochemicals Over Time

| | Days after treatment (30° C.) | | |
|---|---|---|---|
| Treatments | 0 | 2 | 5 |
| 1 | 1.00E+05 | 1.60E+03 | BDL* |
| 2 | 5.40E+05 | 3.50E+05 | 2.30E+04 |
| 3 | 2.80E+05 | 1.20E+05 | 8.00E+03 |

BDL*: Below detection limits ($10^2$ CFU/seed)

As shown in Table 6, the presence of yeast extract and calcium caseinate improve microbial recovery in seeds treated with benzyl hemi-formal containing agrochemicals.

Example 4

The activity of two microbially stabilizing compounds, yeast extract and albumin, were tested for reducing the effects of the preservative benzyl hemi-formal (at a concentration reflecting that provided by the current recommendation for a commercial insecticide that includes that preservative).

Using conventional aseptic techniques, 10 ml of a commercial liquid inoculant containing *B. japonicum* SEMIA 5079 and *B. japonicum* SEMIA 5080 (Nitragin CellTech HC, commercially available from Novozymes) was transferred to a series of sterile test tubes, to which 0.7 ml of a 2% solution containing benzyl hemi-formal was added and, in the corresponding tubes, 0.3 g of Yeast extract (commercially available from Merck) or 0.3 g Albumin (commercially available from SIGMA) were incorporated. A control of bacterial survival consisting of the inoculants without a microbial stabilizing compound was tested for comparison. The treatments are provided in Table 7.

TABLE 7

| Treatment | Inoculant | Benzyl hemi-formal (final concentration) | Yeast extract (final concentration) | Albumin (final concentration |
|---|---|---|---|---|
| 1 | 10 ml | 0.14% w/v | | |
| 2 | 10 ml | 0.14% w/v | 0.03% w/v | |
| 3 | 10 ml | 0.14% w/v | | 0.03% w/v |
| 4 | 10 ml | | | |

The tubes were mixed using a vortex agitator, transferred to a 30° C. orbital shaker. After 20 minutes incubation (Time 0), 0.1 ml samples were taken, and conventionally diluted 1/10 in a series of tubes containing 0.9 ml of sterile saline solution (0.85% NaCl in distilled water). 0.1 ml of dilutions $10^{-5}$, $10^{-6}$ and, $10^{-7}$ were plated in triplicate on Yeast Extract Mannitol Agar (YEM). The plates were incubated at 30° C. Colonies were counted after seven days incubation. The number of colony forming units per ml (CFU $ml^{-1}$) was calculated taking into account the plated dilutions and the plated volume. Samples were obtained and processed as above at two hours intervals. Results are indicated in Table 8.

TABLE 8

Effect of Yeast Extract and Albumin on Inoculant Survivability in the Presence of Benzyl Hemi-Formal Over Time

| Treatment | 0 hs | 2 hs | 4 hs | 6 hs |
|---|---|---|---|---|
| 1 | 3.10E+09 | 1.30E+08 | BDL* | BDL* |
| 2 | 3.80E+09 | 3.30E+09 | 5.00E+08 | 3.10E+08 |
| 3 | 3.70E+09 | 5.10E+08 | 5.50E+07 | 3.10E+07 |
| 4 | 3.40E+09 | 3.10E+09 | 3.00E+09 | 3.30E+09 |

*BDL: Below Detection Limits ($10^6$ CFU/ml)

As shown in Table 8, yeast extract and albumin reduce the deleterious effects induced by the presence of benzyl hemi-formal at the concentration tested.

Example 5

The general protocol described in Example 4 was modified to process larger samples. A commercial insecticide containing benzyl hemi-formal was tested at concentrations that would emulate the recommended doses both for the inoculants and the insecticide.

Sterile 250 ml erlenmeyers containing sterile magnetic stirrers were used instead of test tubes. The volumes of each solution are provided in Table 9. The commercial insecticide was transferred to a series of erlenmeyers and the stated amounts of microbial stabilizing compounds (yeast extract and soy meal peptone from Merck and tryptophan from Ajinomoto) were premixed at 250 rpm for 6 hours.

TABLE 9

Treatments

| Treatment | Inoculant (30 ml) | Insecticide (30 ml) | Yeast extract (3 g) | Peptone from soymeal (3 g) | Tryptophan (1 g) |
|---|---|---|---|---|---|
| 1 | X | X | | | |
| 2 | X | X | X | | |
| 3 | X | X | | X | |
| 4 | X | X | | | X |
| 5 | X | | | | |

To each of the corresponding erlenemeyer flasks, 30 ml of inoculant (as described in example 4) was added, mixed, and samples were obtained immediately and at 2 hr intervals. Samples were processed as described in Example 4. Results are provided in Table 10.

TABLE 10

Effect of Yeast Extract and Peptone from soy meal on Inoculant Survivability in the Presence of Insecticide Containing Benzyl Hemi-Formal Over Time

| | cfu/ml | | | |
|---|---|---|---|---|
| Treatment | 0 hs | 2 hs | 4 hs | 6 hs |
| 1 | 1.00E+09 | 1.00E+08 | BDL* | BDL* |
| 2 | 4.30E+09 | 3.50E+09 | 2.10E+09 | 1.00E+09 |
| 3 | 3.30E+09 | 2.60E+09 | 3.00E+09 | 1.30E+09 |
| 4 | 4.30E+09 | 3.70E+09 | 3.20E+09 | 3.30E+09 |
| 5 | 3.40E+09 | 3.10E+09 | 3.30E+09 | 3.30E+09 |

*BDL: Below detection limits ($10^6$ CFU/ml)

As shown in Table 10, yeast extract, peptone from soy meal, and tryptophan, reduce the deleterious effects induced by the presence of benzyl hemi-formal containing agrochemical on a microbial population.

Example 6

Yeast extract and calcium caseinate were used in a peat based preinoculation system containing B. japonicum SEMIA 5079 and B. japonicum SEMIA 5080 (available from Novozymes) and tested for compatibility with benzyl hemi-formal containing agrochemicals for on seed stability. Seed treatment is done following the protocol described herein.

Yeast extract or calcium caseinate (from Merck) were premixed using magnetic stirrers for 6 hours with the benzyl hemi-formal containing agrochemical. After 6 hours, the seeds were treated. Table 11 describes the seed treatments corresponding to 1 kg seed.

TABLE 11

Treatments

| | Treatment Number | | |
|---|---|---|---|
| | 1 | 2 | 3 |
| Peat based preinoculation system containing B. japonicum SEMIA 5079 and B. japonicum SEMIA 5080 | 8.5 g | 8.5 g | 8.5 g |
| Benzyl hemi-formal containing insecticide | 3 ml | 3 ml | 3 ml |
| Yeast extract | | 0.3 g | |
| Calcium caseinate | | | 0.3 g |

For treatments combining liquid inoculants and other products (fungicides, insecticides, etc), the treatment was prepared according to instructions and let stand at room temperature for half an hour before inoculating seeds.

Seeds were placed inside a polyethylene bag and the treatment was added. The seeds must occupy ⅓ of the total volume of the bag (inflated and closed). The contents of the bag were mixed vigorously with rotating movements for proper distribution of the products inside.

The bag with the inoculated seeds was opened and left to sit at room temperature for 4 hours and on seed rhizobial counts were made. For this, 100 seeds were placed in a 250 ml Erlenmeyer with 100 ml of saline solution and subjected to shaking for 15 min using magnetic stirrer at approximately 300 rpm. The supernatant is named the dilution 10°. 1 ml samples were taken, and conventionally diluted 1/10 in a series of tubes containing 9 ml of sterile saline solution (0.85% NaCl in distilled water). 0.1 ml of dilutions $10^{-1}$, $10^{-2}$, $10^{-3}$ and $10^{-4}$ were plated in triplicate on Yeast Extract Mannitol Agar (YEM).

Seeds were then placed in paper bags and kept in a 30° C. chamber until the end of the test. Determinations were repeated at 24 and 48 hours after inoculation. Plates were read after seven days and checked on day ten. Plates were counted having between 30 and 300 colonies and the ratio between dilutions was checked. The CFU.seed$^{-1}$ according to formula (I) as provided above was calculated. Results are provided in Table 12.

TABLE 12

Effect of Yeast Extract and Calcium Caseinate on On-Seed Microbial Survivability when using Benzyl Hemi-Formal containing agrochemicals Over Time

| Treatments | Days after treatment (30° C.) | | |
|---|---|---|---|
| | 0 | 2 | 5 |
| 1 | 1.50E+05 | 6.60E+03 | BDL* |
| 2 | 3.40E+05 | 3.10E+05 | 2.50E+04 |
| 3 | 3.00E+05 | 1.00E+05 | 7.20E+03 |

BDL*: Below detection limits ($10^2$ CFU/seed)

As shown in Table 12, the presence of yeast extract and calcium caseinate improve microbial recovery in seeds treated with benzyl hemi-formal containing agrochemicals.

It will be understood that the Specification and Examples are illustrative of the present embodiments and that other embodiments within the spirit and scope of the claimed embodiments will suggest themselves to those skilled in the art. Although this disclosure has been described in connection with specific forms and embodiments thereof, it would be appreciated that various modifications other than those discussed above may be resorted to without departing from the spirit or scope of the embodiments as defined in the appended claims. For example, equivalents may be substituted for those specifically described, and in certain cases, particular applications of steps may be reversed or interposed all without departing from the spirit or scope for the embodiments as described in the appended claims.

The invention claimed is:

1. A method for increasing the survivability of microorganisms in a seed treatment composition comprising one or more antimicrobial compounds and one or more beneficial microorganisms, said method comprising adding lecithin to said seed treatment composition in an amount sufficient to inhibit an antimicrobial activity of said one or more antimicrobial compounds, wherein said lecithin may be added to said seed treatment composition prior to, simultaneously with and/or subsequent to the inclusion of said one or more antimicrobial compounds and/or said one or more beneficial microorganisms in said seed treatment composition.

2. The method of claim 1, wherein the one or more beneficial microorganisms comprises one or more nitrogen-fixing microorganisms.

3. The method of claim 1, wherein the one or more beneficial microorganisms comprises one or more phosphate solubilizing microorganisms.

4. The method of claim 1, said method further comprising the step of adding to the seed treatment composition one or more microbially stabilizing compounds selected from the group consisting of yeast extract, calcium caseinate, milk, urea, hematinic agents, beef extract, ammonia, amino acids, ammonium salts, ferric salts, ferrous salts, gluconolactone, glutathione, polysorbates, albumin, peptones, and combinations thereof.

5. The method of claim 1, wherein the one or more antimicrobial compounds comprises a bacteriostat, a bactericide, or a combination thereof.

6. The method of claim 1, wherein the one or more antimicrobial compounds comprises a disinfectant, an antiseptic, or an antibiotic.

7. The method of claim 1, wherein the one or more antimicrobial compounds comprises one or more compounds selected from the group consisting of formaldehyde, benzyl-hemiformal (phenylmethoxymethanol), 2-bromo-2-nitro-1,3-propanediol, 1-(3-chloroallyl)-3,5,7-triaza-1-azoniaadamantane chloride, dibromonitrilopropionamide, 1,2-benzisothiazolin-3-one, 5-chloro-2-methyl-4-isothiazolin-3-one, 2-methyl-4-isothiazolin-3-one, diazolidinyl urea, tris(hydroxymethyl)nitromethane, sodium o-phenylphenate, copper arsenates, cuprous oxide, compounds of arsenic, copper, mercury, quaternary ammonium compounds, sodium azide, thimerosol, active chlorine, active oxygen, iodine, peroxides, organic acids, alcohols, phenolic substances, cationic surfactants, penicillin, cephalosporins, aminoglycosidic antibiotics, fluoroquinolones, nitrofurans, vancomycin, monobactams, co-trimoxazole, metronidazole, and combinations thereof.

8. The method of claim 1, wherein the method further comprises the step of adding to the seed treatment composition one or more agriculturally beneficial ingredients.

9. The method of claim 8, wherein the one or more agriculturally beneficial ingredients comprises one or more plant signal molecules selected from the group consisting of lipo-chitooligosaccharides (LCOs), chitooligosaccharides (COs), chitinous compounds, flavonoids, jasmonic acid, methyl jasmonate, linoleic acid, linolenic acid, karrikins, and combinations thereof.

* * * * *